(12) United States Patent
Tsalik et al.

(10) Patent No.: US 11,286,525 B2
(45) Date of Patent: Mar. 29, 2022

(54) GENE EXPRESSION SIGNATURES USEFUL TO PREDICT OR DIAGNOSE SEPSIS AND METHODS OF USING THE SAME

(71) Applicant: Duke University, Durham, NC (US)

(72) Inventors: Ephraim L. Tsalik, Cary, NC (US); Geoffrey S. Ginsburg, Durham, NC (US); Christopher W. Woods, Durham, NC (US); Ricardo Henao Giraldo, Durham, NC (US); Rachel A. Myers, Raleigh, NC (US)

(73) Assignees: Duke University, Durham, NC (US); United States Government as Represented by the Department of Veterans Affairs, Washington, DC (US)

( * ) Notice: Subject to any disclaimer, the term of this patent is extended or adjusted under 35 U.S.C. 154(b) by 65 days.

(21) Appl. No.: 16/478,202

(22) PCT Filed: Jan. 16, 2018

(86) PCT No.: PCT/US2018/013832
§ 371 (c)(1),
(2) Date: Jul. 16, 2019

(87) PCT Pub. No.: WO2018/140256
PCT Pub. Date: Aug. 2, 2018

(65) Prior Publication Data
US 2020/0157623 A1  May 21, 2020

Related U.S. Application Data

(60) Provisional application No. 62/446,940, filed on Jan. 17, 2017.

(51) Int. Cl.
*C12Q 1/6876* (2018.01)

(52) U.S. Cl.
CPC ...... *C12Q 1/6876* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 10,344,332 B2 * | 7/2019 | Khatri | A61P 37/02 |
| 2009/0203534 A1 | 8/2009 | Hossain et al. | |
| 2011/0312521 A1 | 12/2011 | Chaussabel | |
| 2015/0259746 A1 | 9/2015 | Brandon et al. | |
| 2016/0168638 A1 | 6/2016 | Garrett et al. | |

FOREIGN PATENT DOCUMENTS

| | | |
|---|---|---|
| WO | 2015135071 | 9/2015 |
| WO | 2017004390 | 1/2017 |
| WO | 2018004806 | 1/2018 |

OTHER PUBLICATIONS

Friggeri et al. Critical Care. 2016. 20: 204, p. 1-13 (Year: 2016).*
Almansa et al. J. Infection. 2015. 70: 445-456, and Supplemental Data 2 and 4 (4 pages) (Year: 2015).*
Sweeney, T.E. & Wong, H.R., Risk stratification and prognosis in sepsis: what have we learned from micrarrays?, Clin. Chest Med., vol. 37, No. 2, 2016, pp. 209-2018.
Almansa et al, Transcriptomic correlates of organ failure extent in sepsis, The Journal of Infection, vol. 70, 2015, pp. 445-456, Abstract only.
Wong et al, Developing a Clinically Feasible Personalized Medicine Approach to Pediatric Septic Shock, American Journal of Respiratory and Critical Care Medicine, vol. 191, No. 3, 2015, pp. 309-315.
Davenport et al, Genomic landscape of the individual host response and outcomes in sepsis: a prospective cohort study, Lancet Respir Med, vol. 4, 2016, pp. 259-271.
Parnell et al, Identifying Key Regulatory Genes in the Whole Blood of Septic Patients to Monitor Underlying Immune Dysfunctions, Shock, vol. 40, No. 3, 2013, pp. 166-174.
Parnell et al, Aberrant Cell Cycle and Apoptotic Changes Characterise Severe Influenza A Infection—A Meta-Analysis of Genomic Signatures in Circulating Leukocytes, PLos One, vol. 6, No. 3, 2011, pp. 1-10.
Wong et al, Genome level expression profiles in pediatric septic shock indicate a role for altered zinc homeostasis in poor outcome, Physiol Genomics, vol. 30, No. 2, 2007, pp. 146-155.
Tsalik et al, An integrated transcriptome and expressed variant analysis of sepsis survival and death, Genome Medicine, vol. 6, 2014, pp. 1-15.
International Search Report and Written Opinion corresponding to PCT/US2018/013832, dated Jul. 6, 2018, 12 pages.

* cited by examiner

*Primary Examiner* — Carla J Myers
(74) *Attorney, Agent, or Firm* — Myers Bigel, P.A.

(57) ABSTRACT

The present disclosure provides methods for determining whether a subject has sepsis, or is at risk of developing sepsis, and methods of treating the subject based on the determination. Also provided are methods for determining an increased risk of mortality in a subject with sepsis or suspected of having sepsis, and methods of treating the subject based on the determination. Systems useful for the same are also provided.

6 Claims, 11 Drawing Sheets

GENE EXPRESSION SIGNATURES USEFUL TO PREDICT OR DIAGNOSE SEPSIS AND METHODS OF USING THE SAME

RELATED APPLICATIONS

This application claims the benefit of U.S. Provisional Patent Application Ser. No. 62/446,940, filed Jan. 17, 2017, the disclosure of which is incorporated by reference herein in its entirety.

FEDERAL FUNDING LEGEND

This invention was made with Government Support under Federal Grant Nos. W911NF-15-1-0107 awarded by the DOD/DARPA. The Government has certain rights to this invention.

BACKGROUND

It has been hypothesized that whole-blood transcriptomic (genome-wide expression) profiling may be an effective way to stratify sepsis patients. See Sweeney, T. E. & Wong, H. R. Risk Stratification and Prognosis in Sepsis: What Have We Learned from Microarrays? *Clin. Chest Med.* 37, 209-218 (2016); Almansa, R. et al. Transcriptomic correlates of organ failure extent in sepsis. *J. Infect.* 70, 445-456 (2015); Wong, H. R. et al. Developing a clinically feasible personalized medicine approach to pediatric septic shock. *Am. J. Respir. Grit. Care Med.* 191, 309-315 (2015); Davenport, E. E. et al. Genomic landscape of the individual host response and outcomes in sepsis: a prospective cohort study. *Lancet Respir Med* (2016). doi:10.1016/S2213-2600(16)00046-1.

Important insights from these studies suggest that more severe sepsis is accompanied by an overexpression of neutrophil proteases, adaptive immune exhaustion, and an overall profound immune dysregulation. See Sweeney et al. and Almansa et al., supra; Parnell, G. et al. Aberrant cell cycle and apoptotic changes characterise severe influenza A infection—a meta-analysis of genomic signatures in circulating leukocytes. *PLoS One* 6, e17186 (2011); Parnell, G. P. et al. Identifying key regulatory genes in the whole blood of septic patients to monitor underlying immune dysfunctions. *Shock* 40, 166-174 (2013); Wong, H. R. et al. Genome-level expression profiles in pediatric septic shock indicate a role for altered zinc homeostasis in poor outcome. *Physiol. Genomics* 30, 146-155 (2007); Tsalik, E. L. et al. An integrated transcriptome and expressed variant analysis of sepsis survival and death. *Genome Med.* 6, 111. (2014).

Quantitative evaluation of host response profiles based on these observations have been validated prospectively to show specific outcomes (Wong et al. and Davenport et al., supra), but none have yet been translated into clinical practice. Still, the availability of high-dimensional transcriptomic data from these accumulated studies has created unprecedented opportunities to address questions across heterogeneous representations of sepsis (different ages, pathogens, and patient types) that could not be answered by any individual cohort.

SUMMARY

The present disclosure provides, in part, methods of identify subjects suffering from and/or at risk of developing sepsis. The present disclosure further provides methods of treating the subjects after the determination has been made. We have investigated gene expression data from many patients with sepsis, some of whom survived and some of whom did not. We used that data to identify gene expression signatures, present at the time of initial clinical presentation, that predict survival through 30 days.

Provided herein in some embodiments is a method for determining an increased risk of mortality in a subject with sepsis or suspected of having sepsis, comprising: providing a biological sample of the subject; and measuring on a platform differential expression of a pre-defined set of genes, comprising: i) an increase in expression of one, two, or three or more genes selected from the group consisting of: TRIB1, CKS2, MKI67, POLD3, and PLK1; and/or ii) a decrease in expression of two, three, four or five or more genes selected from the group consisting of: TGFBI, LY86, CST3, CBFA2T3, RCBTB2, TST, CX3CR1, CD5, MTMR11, CLEC10A, EMR3, DHRS7B, and CEACAM8; wherein said subject is identified as having an increased risk of mortality when said i) increase in expression and/or said ii) decrease in expression is present.

In some embodiments, the measuring further comprises measuring differential expression of additional genes selected from those listed in Table 3 and/or Table 4.

In some embodiments, the measuring comprises or is preceded by one or more steps of: purifying cells from said sample, breaking the cells of said sample, and isolating RNA from said sample.

In some embodiments, the measuring comprises semi-quantitative PCR and/or nucleic acid probe hybridization.

In some embodiments, the platform comprises an array platform, a thermal cycler platform (e.g., multiplexed and/or real-time PCR platform), a hybridization and multi-signal coded (e.g., fluorescence) detector platform, a nucleic acid mass spectrometry platform, a nucleic acid sequencing platform, or a combination thereof.

Also provided are methods of treating a subject for sepsis when said subject is identified as having an increased risk of mortality as taught herein.

Further provided are systems for determining an increased risk of mortality in a subject with sepsis or suspected of having sepsis, comprising some or all of: at least one processor; a sample input circuit configured to receive a biological sample from the subject; a sample analysis circuit coupled to the at least one processor and configured to determine gene expression levels of the biological sample of a set of pre-determined genes, said pre-determined genes comprising two, three, four, five, six, seven, eight, nine, or ten or more genes selected from the group consisting of: TRIB1, CKS2, MKI67, POLD3, PLK1, TGFBI, LY86, CST3, CBFA2T3, RCBTB2, TST, CX3CR1, CD5, MTMR11, CLEC10A, EMR3, DHRS7B, and CEACAM8; an input/output circuit coupled to the at least one processor; a storage circuit coupled to the at least one processor and configured to store data, parameters, and/or gene set(s); and a memory coupled to the processor and comprising computer readable program code embodied in the memory that when executed by the at least one processor causes the at least one processor to perform operations comprising: controlling/performing measurement via the sample analysis circuit of gene expression levels of the pre-defined set of genes in said biological sample; normalizing the gene expression levels to generate normalized gene expression values; retrieving from the storage circuit pre-defined weighting values (i.e., coefficients) for each of the genes of the pre-defined set of genes; calculating a probability of mortality due to sepsis based upon weighted values of the normalized gene expression values; and controlling output via the input/output circuit of a determination of mortality risk.

In some embodiments, the system comprises computer readable code to transform quantitative, or semi-quantitative, detection of gene expression to a cumulative score or probability of mortality due to sepsis.

In some embodiments, the system comprises an array platform, a thermal cycler platform (e.g., multiplexed and/or real-time PCR platform), a hybridization and multi-signal coded (e.g., fluorescence) detector platform, a nucleic acid mass spectrometry platform, a nucleic acid sequencing platform, or a combination thereof.

In some embodiments, the pre-defined set of genes comprises from 5 to 100 or 200 genes.

In some embodiments, the pre-defined set of genes comprises one or more genes listed in Table 3 and/or Table 4.

Also provided are methods for determining whether a subject has sepsis or is at risk of developing sepsis, such as ventilator associated pneumonia, comprising: providing a biological sample of the subject; and measuring on a platform differential expression of a pre-defined set of genes, comprising: i) an increase in expression of two, three, four or five or more genes selected from the group consisting of: PCBP1, TMBIM6, LASP1, KLF2, OS9, APMAP, CD14, NAMPT, NQO2, CDK5RAP2; and/or ii) a decrease in expression of two, three, four or five or more genes selected from the group consisting of: SIGLEC10, TSC22D3, RCN3, LST1, HBA1, FGR, TYMP, ATG16L2, CEACAM4, PECAM1, HMHA1, APOBEC3A, P2RX1; wherein said subject is identified as having sepsis or at risk of developing sepsis when said i) increase in expression and/or said ii) decrease in expression is present.

In some embodiments, the measuring comprises or is preceded by one or more steps of: purifying cells from said sample, breaking the cells of said sample, and isolating RNA from said sample.

In some embodiments, the measuring comprises semi-quantitative PCR and/or nucleic acid probe hybridization.

In some embodiments, the platform comprises an array platform, a thermal cycler platform (e.g., multiplexed and/or real-time PCR platform), a hybridization and multi-signal coded (e.g., fluorescence) detector platform, a nucleic acid mass spectrometry platform, a nucleic acid sequencing platform, or a combination thereof.

Also provided are methods of treating sepsis, such as ventilator associated pneumonia, in a subject in need thereof comprising administering to said subject an appropriate treatment regimen based on determining whether a subject has sepsis or is at risk of developing sepsis as taught herein.

Further provided are systems for determining whether a subject has sepsis or is at risk of developing sepsis, such as ventilator associated pneumonia, comprising some or all of: at least one processor; a sample input circuit configured to receive a biological sample from the subject; a sample analysis circuit coupled to the at least one processor and configured to determine gene expression levels of the biological sample of a set of pre-determined genes, said pre-determined genes comprising two, three, four, five, six, seven, eight, nine, or ten or more genes selected from the group consisting of: PCBP1, TMBIM6, LASP1, KLF2, OS9, APMAP, CD14, NAMPT, NQO2, CDK5RAP2, SIGLEC10, TSC22D3, RCN3, LST1, HBA1, FGR, TYMP, ATG16L2, CEACAM4, PECAM1, HMHA1, APOBEC3A, and P2RX1; an input/output circuit coupled to the at least one processor; a storage circuit coupled to the at least one processor and configured to store data, parameters, and/or gene set(s); and a memory coupled to the processor and comprising computer readable program code embodied in the memory that when executed by the at least one processor causes the at least one processor to perform operations comprising: controlling/performing measurement via the sample analysis circuit of gene expression levels of the pre-defined set of genes in said biological sample; normalizing the gene expression levels to generate normalized gene expression values; retrieving from the storage circuit pre-defined weighting values (i.e., coefficients) for each of the genes of the pre-defined set of genes; calculating a probability of sepsis based upon weighted values of the normalized gene expression values; and controlling output via the input/output circuit of a determination of sepsis.

In some embodiments, the computer readable code to transform quantitative, or semi-quantitative, detection of gene expression to a cumulative score or probability of the sepsis.

In some embodiments, the system comprises an array platform, a thermal cycler platform (e.g., multiplexed and/or real-time PCR platform), a hybridization and multi-signal coded (e.g., fluorescence) detector platform, a nucleic acid mass spectrometry platform, a nucleic acid sequencing platform, or a combination thereof.

In some embodiments, the pre-defined set of genes comprises from 5 to 100 or 200 genes.

Also provided is the use of an appropriate treatment for sepsis in a subject determined to have sepsis, or to have an increased risk of mortality, as taught herein.

Yet another aspect of the present disclosure provides all that is disclosed and illustrated herein.

BRIEF DESCRIPTION OF THE DRAWINGS

The foregoing aspects and other features of the disclosure are explained in the following description, taken in connection with the accompanying drawings, herein.

DETAILED DESCRIPTION

Figure 1:
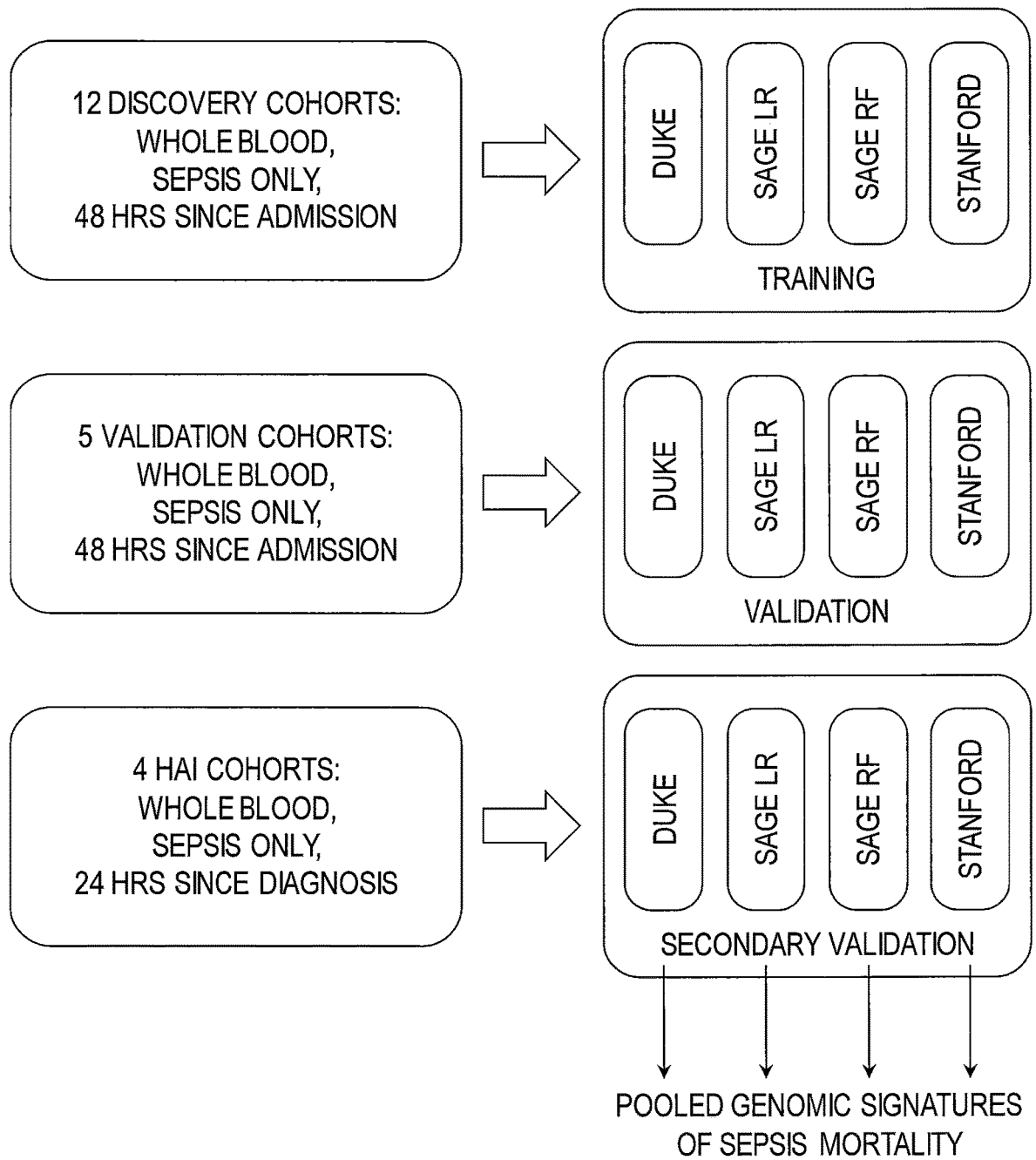
FIG. 1 is an overview of analysis in accordance with one embodiment of the present disclosure, and provides schema of federated multi-cohort analysis with the three phases: (i) Discovery, (ii) Validation, and (iii) Secondary validation (HAI cohorts).

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The term "subject" and "patient" are used interchangeably and refer to any animal being examined, studied or treated. It is not intended that the present disclosure be limited to any particular type of subject. In some embodiments of the present invention, humans are the preferred subject, while in other embodiments non-human animals are the preferred subject, including, but not limited to, mice, monkeys, ferrets, cattle, sheep, goats, pigs, chicken, turkeys, dogs, cats, horses and reptiles. In certain embodiments, the subject is suffering from sepsis or is displaying symptoms of sepsis.

"Platform" or "technology" as used herein refers to an apparatus (e.g., instrument and associated parts, computer, computer-readable media comprising one or more databases as taught herein, reagents, etc.) that may be used to measure a signature, e.g., gene expression levels, in accordance with the present disclosure. Examples of platforms include, but are not limited to, an array platform, a thermal cycler platform (e.g., multiplexed and/or real-time PCR or RT-PCR platform), a nucleic acid sequencing platform, a hybridization and multi-signal coded (e.g., fluorescence or light scattering from nanoparticles such as gold nanoparticles) detector platform, etc., a nucleic acid mass spectrometry platform, a magnetic resonance platform, and combinations thereof.

In some embodiments, the platform is configured to measure gene expression levels semi-quantitatively, that is, rather than measuring in discrete or absolute expression, the expression levels are measured as an estimate and/or relative to each other or a specified marker or markers (e.g., expression of another, "standard" or "reference," gene).

In some embodiments, semi-quantitative measuring includes "real-time PCR" by performing PCR cycles until a signal indicating the specified mRNA is detected, and using the number of PCR cycles needed until detection to provide the estimated or relative expression levels of the genes within the signature.

A real-time PCR platform includes, for example, a TaqMan® Low Density Array (TLDA), in which samples undergo multiplexed reverse transcription, followed by real-time PCR on an array card with a collection of wells in which real-time PCR is performed. See Kodani et al. 2011, *J. Clin. Microbiol.* 49(6):2175-2182. A real-time PCR platform also includes, for example, a Biocartis Idylla™ sample-to-result technology, in which cells are lysed, DNA/RNA extracted and real-time PCR is performed and results detected.

A magnetic resonance platform includes, for example, T2 Biosystems® T2 Magnetic Resonance (T2MR®) technology, in which molecular targets may be identified in biological samples without the need for purification.

The terms "array," "microarray" and "micro array" are interchangeable and refer to an arrangement of a collection of nucleotide sequences presented on a substrate. Any type of array can be utilized in the methods provided herein. For example, arrays can be on a solid substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. See, e.g., Luminex Verigene® System, which uses gold nanoparticle probe technology. Magnetic nanoparticles may also be used. Other examples include nuclear magnetic resonance microcoils. The nucleotide sequences can be DNA, RNA, or any permutations thereof (e.g., nucleotide analogues, such as locked nucleic acids (LNAs), and the like). In some embodiments, the nucleotide sequences span exon/intron boundaries to detect gene expression of spliced or mature RNA species rather than genomic DNA. The nucleotide sequences can also be partial sequences from a gene, primers, whole gene sequences, non-coding sequences, coding sequences, published sequences, known sequences, or novel sequences. The arrays may additionally comprise other compounds, such as antibodies, peptides, proteins, tissues, cells, chemicals, carbohydrates, and the like that specifically bind proteins or metabolites.

An array platform includes, for example, the TaqMan® Low Density Array (TLDA) mentioned above, and an Affymetrix® microarray platform.

A hybridization and multi-signal coded detector platform includes, for example, NanoString nCounter® technology, in which hybridization of a color-coded barcode attached to a target-specific probe (e.g., corresponding to a gene expression transcript of interest) is detected; and Luminex® xMAP® technology, in which microsphere beads are color coded and coated with a target-specific (e.g., gene expression transcript) probe for detection; the Luminex Verigene® System that uses gold nanoparticle probes, and Illumina® BeadArray, in which microbeads are assembled onto fiber optic bundles or planar silica slides and coated with a target-specific (e.g., gene expression transcript) probe for detection.

A nucleic acid mass spectrometry platform includes, for example, the Ibis Biosciences Plex-ID® Detector, in which DNA mass spectrometry is used to detect amplified DNA using mass profiles.

A thermal cycler platform includes, for example, the FilmArray® multiplex PCR system, which extract and purifies nucleic acids from an unprocessed sample and performs nested multiplex PCR; the RainDrop Digital PCR System, which is a droplet-based PCR platform using microfluidic chips; or the Qvella FAST™ system to lyse blood cells, in addition to lysing pathogens, to generate a PCR-ready lysate.

The term "computer readable medium" refers to any device or system for storing and providing information (e.g., data and instructions) to a computer processor. Examples of computer readable media include, but are not limited to, DVDs, CDs hard disk drives, magnetic tape and servers for streaming media over networks, and applications, such as those found on smart phones and tablets. In various embodiments, aspects of the present invention including data structures and methods may be stored on a computer readable medium. Processing and data may also be performed on numerous device types, including but not limited to, desk top and lap top computers, tablets, smart phones, and the like.

As used herein, the term "biological sample" comprises any sample that may be taken from a subject that contains genetic material that can be used in the methods provided herein. For example, a biological sample may comprise a peripheral blood sample. The term "peripheral blood sample" refers to a sample of blood circulating in the circulatory system or body taken from the system of body. Other samples may comprise those taken from the upper respiratory tract, including but not limited to, sputum, nasopharyngeal swab and nasopharyngeal wash. A biological sample may also comprise those samples taken from the lower respiratory tract, including but not limited to, bronchoalveolar lavage and endotracheal aspirate. A biological sample may also comprise any combinations thereof.

In some embodiments, the sample is not purified after collection. In some embodiments, the sample may be purified to remove extraneous material, before or after lysis of cells. In some embodiments, the sample is purified with cell lysis and removal of cellular materials, isolation of nucleic acids, and/or reduction of abundant transcripts such as globin or ribosomal RNAs.

The term "genetic material" refers to a material used to store genetic information in the nuclei or mitochondria of an organism's cells. Examples of genetic material include, but are not limited to, double-stranded and single-stranded DNA, cDNA, RNA, and mRNA.

The term "plurality of nucleic acid oligomers" refers to two or more nucleic acid oligomers, which can be DNA or RNA.

As used herein, the terms "treat", "treatment" and "treating" refer to the reduction or amelioration of the severity, duration and/or progression of a disease or disorder such as sepsis, or one or more symptoms thereof resulting, from the administration of one or more therapies.

The term "effective amount" refers to an amount of a therapeutic agent that is sufficient to exert a physiological effect in the subject.

The term "appropriate treatment regimen" refers to the standard of care needed to treat a specific disease or disorder. Often such regimens require the act of administering to a subject a therapeutic agent(s) in an effective amount. For example, a therapeutic agent for treating a subject having sepsis may include an antibiotic, which include, but are not limited to, penicillins, cephalosporins, fluroquinolones, tetracyclines, macrolides, and aminoglycosides. In some embodiments, treatment for sepsis may include hydration, including but not limited to normal saline, lactated ringers solution, or osmotic solutions such as albumin. Treatment for sepsis may also include transfusion of blood products or the administration of vasopressors including but not limited to norepinephrine, epinephrine, dopamine, vasopressin, or dobutamine. Some patients with sepsis will have respiratory failure and may require ventilator assistance including but not limited to biphasic positive airway pressure or intubation and ventilation. The appropriate treatment regimen also includes the overall level of care and monitoring. Some patients may be monitored and treated in the Emergency Department with rapid improvement, some may require hospitalization in a routine hospital care unit, and some may require care in an intensive care unit, which is dictated by the severity of illness.

The methods and assays of the present disclosure may be based upon gene expression, for example, through direct measurement of RNA, measurement of derived materials (e.g., cDNA), and measurement of RNA products (e.g., encoded proteins or peptides). Any method of extracting and screening gene expression may be used and is within the scope of the present disclosure.

In some embodiments, the measuring comprises the detection and quantification (e.g., semi-quantification) of mRNA in the sample. In some embodiments, the gene expression levels are adjusted relative to one or more standard gene level(s) ("normalized"). As known in the art, normalizing is done to remove technical variability inherent to a platform to give a quantity or relative quantity (e.g., of expressed genes).

In some embodiments, detection and quantification of mRNA may first involve a reverse transcription and/or amplification step, e.g., RT-PCR such as quantitative RT-PCR. In some embodiments, detection and quantification may be based upon the unamplified mRNA molecules present in or purified from the biological sample. Direct detection and measurement of RNA molecules typically involves hybridization to complementary primers and/or labeled probes. Such methods include traditional northern blotting and surface-enhanced Raman spectroscopy (SERS), which involves shooting a laser at a sample exposed to surfaces of plasmonic-active metal structures with gene-specific probes, and measuring changes in light frequency as it scatters.

Similarly, detection of RNA derivatives, such as cDNA, typically involves hybridization to complementary primers and/or labeled probes. This may include high-density oligonucleotide probe arrays (e.g., solid state microarrays and bead arrays) or related probe-hybridization methods, and polymerase chain reaction (PCR)-based amplification and detection, including real-time, digital, and end-point PCR methods for relative and absolute quantitation of specific RNA molecules.

Additionally, sequencing-based methods can be used to detect and quantify RNA or RNA-derived material levels. When applied to RNA, sequencing methods are referred to as RNAseq, and provide both qualitative (sequence, or presence/absence of an RNA, or its cognate cDNA, in a sample) and quantitative (copy number) information on RNA molecules from a sample. See, e.g., Wang et al. 2009 Nat. Rev. Genet. 10(1):57-63. Another sequence-based method, serial analysis of gene expression (SAGE), uses cDNA "tags" as a proxy to measure expression levels of RNA molecules.

Moreover, use of proprietary platforms for mRNA detection and quantification may also be used to complete the methods of the present disclosure. Examples of these are Pixel™ System, incorporating Molecular Indexing™, developed by CELLULAR RESEARCH, INC., NanoString® Technologies nCounter gene expression system; mRNA-Seq, Tag-Profiling, BeadArray™ technology and VeraCode from Illumina, Luminex VERTGENE® technology, the ICEPlex System from PrimeraDx, the FAST™ system from Qvella, and the QuantiGene 2.0 Multiplex Assay from Affymetrix.

As an example, RNA from whole blood from a subject can be collected using RNA preservation reagents such as PAXgene™ RNA tubes (PreAnalytiX, Valencia, Calif.). The RNA can be extracted using a standard PAXgene™ or Versagene™ (Gentra Systems, Inc, Minneapolis, Minn.) RNA extraction protocol. The Versagene™ kit produces greater yields of higher quality RNA from the PAXgene™ RNA tubes. Following RNA extraction, one can use GLOBINClear™ (Ambion, Austin, Tex.) for whole blood globin reduction. (This method uses a bead-oligonucleotide construct to bind globin mRNA and, in our experience, we are able to remove over 90% of the globin mRNA.) Depending on the technology, removal of abundant and non-interesting transcripts may increase the sensitivity of the assay, such as with a microarray platform.

Quality of the RNA can be assessed by several means. For example, RNA quality can be assessed using an Agilent 2100 Bioanalyzer immediately following extraction. This analysis provides an RNA Integrity Number (RIN) as a quantitative measure of RNA quality. Also, following globin reduction the samples can be compared to the globin-reduced standards. In addition, the scaling factors and background can be assessed following hybridization to microarrays.

Real-time PCR may be used to quickly identify gene expression from a whole blood sample. For example, the isolated RNA can be reverse transcribed and then amplified and detected in real time using non-specific fluorescent dyes that intercalate with the resulting ds-DNA, or sequence-specific DNA probes labeled with a fluorescent reporter which permits detection only after hybridization of the probe with its complementary DNA target.

Hence, it should be understood that there are many methods of mRNA quantification and detection that may be used by a platform in accordance with the methods disclosed herein.

The expression levels are typically normalized following detection and quantification as appropriate for the particular platform using methods routinely practiced by those of ordinary skill in the art.

Sepsis, recently defined as organ dysfunction caused by a dysregulated host response to infection (Singer, M. et al. The Third International Consensus Definitions for Sepsis and Septic Shock (Sepsis-3). JAMA 315, 801 (2016)), contributes to half of all in-hospital deaths in the US and is the leading cost for the US healthcare system. See Torio, C. M. (ahrq) & Andrews, R. M. (ahrq). National Inpatient Hospital Costs: The Most Expensive Conditions by Payer, 2011. HCUP Statistical Brief #160. (2013); Liu, V. et al. Hospital Deaths in Patients With Sepsis From 2 Independent Cohorts. JAMA (2014). doi:10.1001/jama.2014.5804. Although sepsis outcomes have improved over the last decade with standardized sepsis care, mortality rates remain high (10-35%). See Kaukonen, K. M., Bailey, M., Pilcher, D., Cooper, D. J. & Bellomo, R. Systemic inflammatory response syndrome criteria in defining severe sepsis. N. Engl. J. Med. 372, 1629-1638 (2015). Sepsis treatment still focuses on general management strategies including source control, antibiotics, and supportive care. Despite dozens of clinical trials, no treatment specific for sepsis has been successfully utilized in clinical practice. See Opal, S. M., Dellinger, R. P., Vincent, J. L., Masur, H. & Angus, D. C. The next generation of sepsis clinical trial designs: what is next after the demise of recombinant human activated protein C?*. Crit. Care Med. 42, 1714-1721 (2014).

Two consensus papers suggest that continued failure of proposed sepsis therapies is due to substantial patient heterogeneity in the sepsis syndrome and a lack of tools to accurately categorize sepsis at the molecular level. Opal et al., supra, and Cohen, J. et al. Sepsis: a roadmap for future research. *Lancet Infect. Dis.* 15, 581-614 (2015). Current tools for risk stratification include clinical severity scores such as APACHE or SOFA as well as blood lactate levels. While these measures assess overall illness severity, they do not adequately quantify the patient's dysregulated response to the infection and therefore fail to achieve the personalization necessary to improve sepsis care. See Shankar-Hari, M. et al. Developing a New Definition and Assessing New Clinical Criteria for Septic Shock: For the Third International Consensus Definitions for Sepsis and Septic Shock (Sepsis-3). JAMA 315, 775-787 (2016).

A molecular definition of the severity of the host response in sepsis provides several benefits. Knowing the severity of sepsis, which is mediated by the host response, can guide a number of treatment decisions. Defining sepsis severity is a task that should be performed at the time of diagnosis and throughout the course of treatment. However, the severity is often unknown until after terminal events have transpired. For example, 30-day mortality can be used as a proxy for sepsis severity during the patient's treatment even though the sepsis may not have been particularly severe at initial presentation. Specific examples of how defining sepsis severity by way of the host response are as follows: First, improved accuracy in sepsis prognosis would improve clinical care through appropriate matching of patients with resources: the very sick can be diverted to ICU for maximal intervention, while patients predicted to have a better outcome may be safely watched in the hospital ward or discharged early. Second, more precise estimates of prognosis would allow for better discussions regarding patient preferences and the utility of aggressive interventions. Third, better molecular phenotyping of sepsis patients has the potential to improve clinical trials through both (1) patient selection and prognostic enrichment for drugs and interventions (e.g., excluding patients predicted to have good vs. bad outcomes), and (2) better assessments of observed-to-expected ratios for mortality. Finally, as a direct quantitative measure of the dysregulation of the host response, molecular biomarkers could potentially help form a quantitative diagnosis of sepsis as distinct from non-septic acute infections. See Abraham, E. New Definitions for Sepsis and Septic Shock: Continuing Evolution but With Much Still to Be Done. JAMA 315, 757-759 (2016). Thus, overall, such a test for sepsis could be a significant asset to clinicians if deployed as a rapid assay.

As an exemplar of sepsis, ventilator-associated pneumonia (VAP) represents a clinical, epidemiological and financial healthcare challenge. As with many forms of sepsis, the current state of diagnostics is highly limited by the heterogeneous patient population and difficulty in distinguishing VAP from the many other complications critically ill patients may experience. As such, the diagnosis of VAP and other forms of sepsis has generally been made on clinical grounds. Serial biomarker measurements such as with procalcitonin and sTREM-1 (soluble triggering receptor expressed on myeloid cells) led to initial hope for a more reliable VAP diagnostic, but studies have shown them to be poorly reliable.

To address this need, we have performed a prospective, multi-site, clinical study to enroll patients at high risk of sepsis, in particular patients recently placed on mechanical ventilation. Patients were sampled serially, before, during, and after an infection was diagnosed. Whole blood and other samples (serum, plasma, urine, etc.) were processed and gene expression data, proteomics, and metabolomics data were generated. From these patients as well as other infection databases, we identified transcriptomic signatures present at the time of infection that could be detected before the onset of infection as well.

Transcription-based modeling has been deployed across many diseases to improve prognostic accuracy. These are typically developed in a method-specific manner using data collected from single cohorts. As a result, prognostic models often lack the generalizability that is necessary to confer utility in clinical applications. See Bolignano, D. et al. Prognostic models in the clinical arena. Aging Clin. Exp. Res. 24, 300-304 (2012). In contrast, community modeling approaches (where multiple groups create models using the same training data) can provide an opportunity to explicitly evaluate predictive performance across a diverse collection of prognostic models sampled from across a broad solution space. See Guinney, J. et al. Prediction of overall survival for patients with metastatic castration-resistant prostate cancer: development of a prognostic model through a crowdsourced challenge with open clinical trial data. Lancet Oncol. (2016). doi:10.1016/S1470-2045(16)30560-5; Sieberts, S. K. et al. Crowdsourced assessment of common genetic contribution to predicting anti-TNF treatment response in rheumatoid arthritis. Nat. Commun. 7, 12460 (2016); Allen, G. I. et al. Crowdsourced estimation of cognitive decline and resilience in Alzheimer's disease. Alzheimers. Dement. 12, 645-653 (2016); Noren, D. P. et al. A Crowdsourcing Approach to Developing and Assessing Prediction Algorithms for AML Prognosis. PLoS Comput. Biol. 12, e1004890 (2016); Saez-Rodriguez, J. et al. Crowdsourcing biomedical research: leveraging communities as innovation engines. Nat. Rev. Genet. 17, 470-486 (2016).

Sepsis is a syndrome representing the maladaptive interaction between host and pathogen. Current mechanisms to identify and characterize patients with sepsis are limited. In particular, they frequently fail to identify patients at high risk of clinical deterioration and death.

To address this problem, a large collection of both public and privately-held gene expression data from clinical sepsis studies at the time of sepsis diagnosis was systematically identified. We then developed a data-driven prognostic model using a comprehensive survey of available data, including 21 different sepsis cohorts (both community acquired and hospital-acquired, N=1,113 patients) to predict 30-day mortality.

The methods we used to generate this discovery involved a two-step process for identifying signatures of mortality in patients with sepsis. The first step consists of a discriminative factor model that attempts to jointly estimate the covariance structure of the data from a low-rank representation consisting of sparse factors, while also producing a sparse predictive model of mortality based on the latent factor scores also estimated by the model. The model has a clear interpretation by virtue of its sparseness property, each factor defines a subset of genes and the predictive model identifies which factors are discriminative (associated) with mortality. In addition, since the model captures the covariance structure of the data, factors not associated with mortality can often be found to be associated with other large sources of variation such as batch effects and/or demographic features. One known disadvantage of sparse factor models is that although it produces sparse factors, the size of the factors is usually in the hundreds of genes, which is less than ideal in applications were translation to targeted platforms admittedly require small gene signatures.

The second step of our methodology consists of down-selecting from the subset(s) of genes deemed by the factor model as discriminative of mortality, we call this collection of genes our core set. To this end, we perform univariate testing (1-way ANOVA) on each of the genes in the core set, individually for each discovery set to better quantify within-cohort mortality associations. Next, we filter-out genes not statistically significant in a proportion of the discovery sets (25% or 3 studies in the experiments) to then optimize the gene signature by greedy forward search on the remaining genes while sorting them by maximum raw p-value across discovery cohorts. The best signature is one such that the weighted average AUC is maximum. The prediction rule of our final predictive model is parameter-free and it is defined as the geometric mean of the up-regulated genes minus the geometric mean of the down-regulated genes in the original scale of the data, i.e., prior log-transformation. Note that this prediction rule is used during the greedy search but is not part of the sparse predictive model of our factor model. We opted for a parameter-free prediction rule as opposed to a parametric model, e.g., logistic regression, to simplify the final model and to make it less dependent on the scale of the data.

We applied this method to identify gene signatures associated with mortality in patients with sepsis. The model estimated 16 factors from which only two were statistically significant with respect to survival status at FDR<0.05. This discriminative factor consisted of 369 genes that form our signature core set. In order to obtain a smaller signature and a parameter-free classification model, we performed univariate testing on each one of the 12 discovery sets while restricting genes to our core set. We discarded genes that were not statistically significant at the p<0.05 level in at least 3 discovery sets (84 of 369). Next we optimized the gene signature by greedy search on the remaining 84 genes sorted by raw p-value across cohorts and using AUC as the performance metric. The greedy algorithm resulted in a final 18 gene set down-selected from the original 84 core set, from which 6 were up-regulated in non-survivors (CEACAM8, TRIB1, CKS2, MKI67, POLD3 and PLK1), while 12 were down-regulated in non-survivors (TGFBI, LY86, CST3, CBFA2T3, RCBTB2, TST, CX3CR1, CD5, MTMR11, CLEC10A, EMR3 and DHRS7B). Prediction of outcomes up to 30 days after the time of sampling represents a difficult task, given that the model must account for all interventions that occur as part of the disease course. An accuracy of 100% is likely not achievable but also not desirable, as it would suggest that mortality is pre-determined and independent of clinical care. Given this background, our prognostic accuracy may represent an upper bound on transcriptomic-based prediction of sepsis outcomes.

In addition, since prognostic accuracy was retained across broad clinical phenotypes (children and adults, with bacterial and viral sepsis, with community-acquired and hospital-acquired infections, from multiple institutions around the world) the model appears to have successfully incorporated the broad clinical heterogeneity of sepsis. Sepsis remains difficult to define. The most recent definition of sepsis groups or "endotypes" of sepsis has already been successfully applied to both pediatric and adult sepsis populations.

For ventilator-associated pneumonia, the top performing model (mean expression) achieved a training AUC of 0.834. The optimized algorithm resulted in a downselected final 24 gene set. Of these 14 were down regulated in VAP (SIGLEC10, TSC22D3, RCN3, LST1, HBA1, FGR, TYMP, ATG16L2, CEACAM4, TYMP (alt. transcript), PECAM1, HMHA1, APOBEC3A, P2RX1) and 10 (PCBP1, TMBIM6, LASP1, KLF2, OS9, APMAP, CD14, NAMPT, NQO2, CDK5RAP2) were upregulated. We then assessed the behavior of the classifier over time. We first retrained the classifier using all training data. AUC for VAP at 1-2 days pre-infection was 0.766 and 1-2 days post-infection was 0.899. Over time there was resolution of the signature.

| Gene name/ HGNC Symbol | Direction of expression change | Ensemble ID | Entrez RefSeq Gene ID | RefSeq (mRNA) | mRNA encoding |
| --- | --- | --- | --- | --- | --- |
| TRIB1 | down | ENSG00000173334 | 10221 | NM_001282985; NM_025195 | tribbles pseudokinase 1 |
| CKS2 | down | ENSG00000123975 | 1164 | NM_001827 | CDC28 protein kinase regulatory subunit 2 |
| MKI67 | down | ENSG00000148773 | 4288 | NM_001145966; NM_002417 | marker of proliferation Ki-67 |
| POLD3 | down | ENSG00000077514 | 10714 | NM_006591 | DNA polymerase delta 3, accessory subunit |
| PLK1 | down | ENSG00000166851 | 5347 | NM_005030 | polo like kinase 1 |
| TGFBI | up | ENSG00000120708 | 7045 | NM_000358 | transforming growth factor beta induced |
| LY86 | up | ENSG00000112799 | 9450 | NM_004271 | lymphocyte antigen 86 |
| CST3 | up | ENSG00000101439 | 1471 | NM_001288614; NM_000099 | Cystatin C |
| CBFA2T3 | up | ENSG00000129993 | 863 | NM_005187; NM_175931 | CBFA2/RUNX1 translocation partner 3 |
| RCBTB2 | up | ENSG00000136161 | 1102 | NM_001268; NM_001286830; NM_001286831; NM_001286832 | RCC1 and BTB domain containing protein 2 |
| TST | up | ENSG00000128311 | 7263 | NM_003312; NM_001270483 | thiosulfate sulfurtransferase |
| CX3CR1 | up | ENSG00000168329 | 1524 | NM_001171171; NM_001171172; NM_001171174; NM_001337 | C-X3-C motif chemokine receptor 1 |
| CD5 | up | ENSG00000110448 | 921 | NM_014207 | CD5 molecule |
| MTMR11 | up | ENSG00000014914 | 10903 | NM_001145862; NM_181873 | myotubularin related protein 11 |
| CLEC10A | up | ENSG00000132514 | 10462 | NM_182906; NM_001330070; NM_006344 | C-type lectin domain containing 10A |
| EMR3 | up | ENSG00000131355 | 84656 | NM_001289158; NM_001289159; NM_032571; NM_152939 | EGF-like module-containing mucin-like hormone receptor-like 3 |
| DHRS7B | up | ENSG00000109016 | 25979 | NM_015510; NM_001330159 | Dehydrogenase/reductase (SDR family) member 7B |
| CEACAM8 | down | ENSG00000124469 | 1088 | NM_001816 | Carcinoembryonic antigen-related cell adhesion molecule 8 |

(Sepsis-3) requires the presence organ dysfunction as measured by an increase in SOFA of two or more points over baseline. Determining the SOFA score can help guide which organ systems are dysfunctional, but this fails to characterize the biological changes are driving the septic response. Molecular tools like the one developed here provide a simple, informative prognosis for sepsis by improving patient risk stratification. Host response profiles could also help to classify patients with sepsis as opposed to non-septic acute infections. Identifying such high-risk patients may also lead to greater success in clinical trials through improved enrichment strategies. This identification of sub- Classification Systems With reference to FIG. 10, a classification system and/or computer program product 1100 may be used in or by a platform, according to various embodiments described herein. A classification system and/or computer program product 1100 may be embodied as one or more enterprise, application, personal, pervasive and/or embedded computer systems that are operable to receive, transmit, process and store data using any suitable combination of software, firmware and/or hardware and that may be standalone and/or interconnected by any conventional, public and/or private, real and/or virtual, wired and/or wireless network including all or a portion of the global communication network known as the Internet, and may include various types of tangible, non-transitory computer readable medium.

Figure 10:
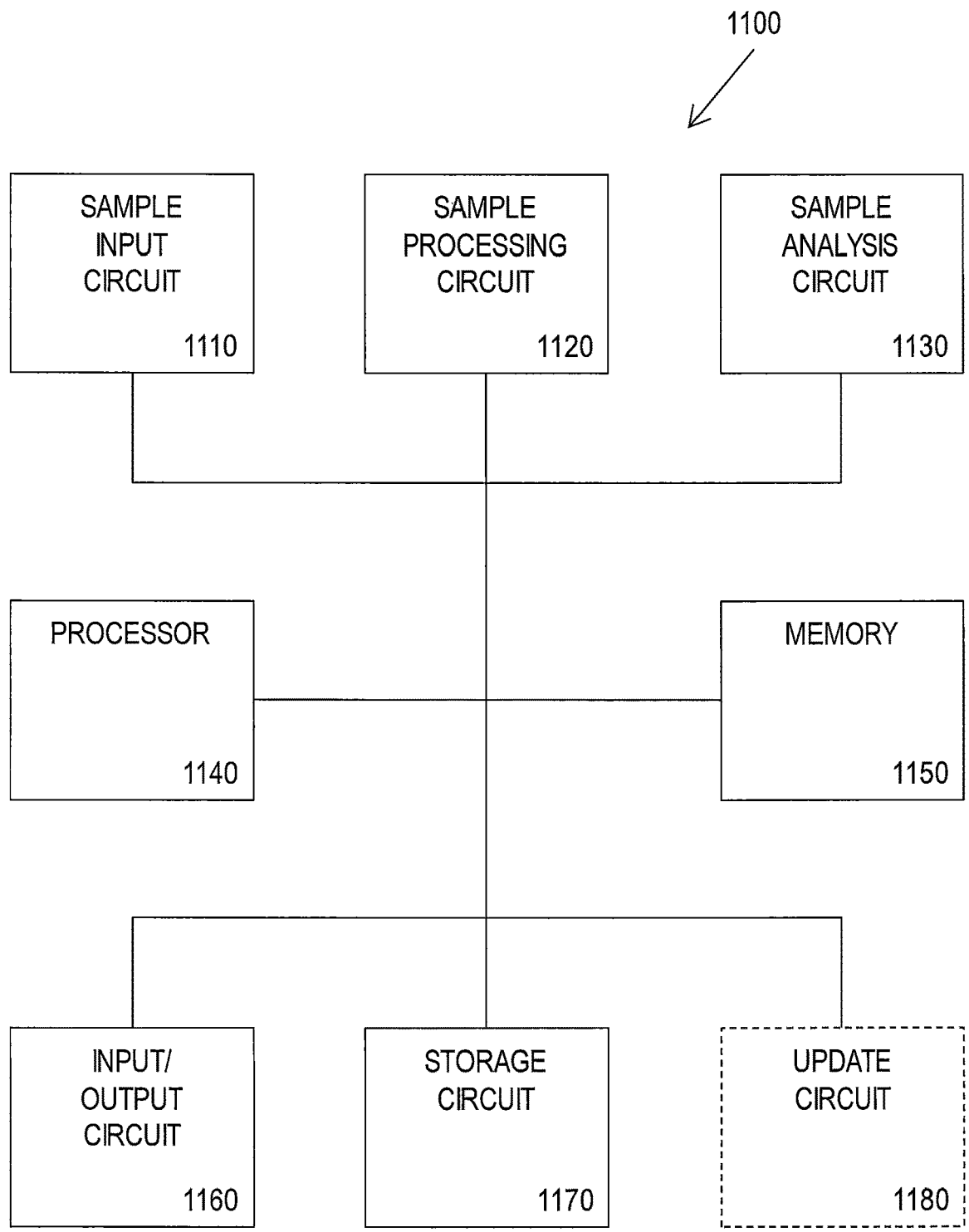
FIG. 10 is a block diagram of a classification system and/or computer program product that may be used in a platform. A classification system and/or computer program product 1100 may include a processor subsystem 1140, including one or more Central Processing Units (CPU) on which one or more operating systems and/or one or more applications run. While one processor 1140 is shown, it will be understood that multiple processors 1140 may be present, which may be either electrically interconnected or separate. Processor(s) 1140 are configured to execute computer program code from memory devices, such as memory 1150, to perform at least some of the operations and methods described herein. The storage circuit 1170 may store databases which provide access to the data/parameters/gene set(s) used by the classification system 1110 such as the signatures, weights, thresholds, etc. An input/output circuit 1160 may include displays and/or user input devices, such as keyboards, touch screens and/or pointing devices. Devices attached to the input/output circuit 1160 may be used to provide information to the processor 1140 by a user of the classification system 1100. Devices attached to the input/output circuit 1160 may include networking or communication controllers, input devices (keyboard, a mouse, touch screen, etc.) and output devices (printer or display). An optional update circuit 1180 may be included as an interface for providing updates to the classification system 1100 such as updates to the code executed by the processor 1140 that are stored in the memory 1150 and/or the storage circuit 1170. Updates provided via the update circuit 1180 may also include updates to portions of the storage circuit 1170 related to a database and/or other data storage format which maintains information for the classification system 1100, such as the signatures, weights, thresholds, etc. The sample input circuit 1110 provides an interface for the classification system 1100 to receive biological samples to be analyzed. The sample processing circuit 1120 may further process the biological sample within the classification system 1100 so as to prepare the biological sample for automated analysis.

As shown in FIG. 10, the classification system 1100 may include a processor subsystem 1140, including one or more Central Processing Units (CPU) on which one or more operating systems and/or one or more applications run. While one processor 1140 is shown, it will be understood that multiple processors 1140 may be present, which may be either electrically interconnected or separate. Processor(s) 1140 are configured to execute computer program code from memory devices, such as memory 1150, to perform at least some of the operations and methods described herein, and may be any conventional or special purpose processor, including, but not limited to, digital signal processor (DSP), field programmable gate array (FPGA), application specific integrated circuit (ASIC), and multi-core processors.

The memory subsystem 1150 may include a hierarchy of memory devices such as Random Access Memory (RAM), Read-Only Memory (ROM), Erasable Programmable Read-Only Memory (EPROM) or flash memory, and/or any other solid state memory devices.

A storage circuit 1170 may also be provided, which may include, for example, a portable computer diskette, a hard disk, a portable Compact Disk Read-Only Memory (CDROM), an optical storage device, a magnetic storage device and/or any other kind of disk- or tape-based storage subsystem. The storage circuit 1170 may provide non-volatile storage of data/parameters/gene set(s) for the classification system 1100. The storage circuit 1170 may include disk drive and/or network store components. The storage circuit 1170 may be used to store code to be executed and/or data to be accessed by the processor 1140. In some embodiments, the storage circuit 1170 may store databases which provide access to the data/parameters/gene set(s) used for the classification system 1110 such as the pre-determined set of genes, weights, thresholds, etc. Any combination of one or more computer readable media may be utilized by the storage circuit 1170. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. As used herein, a computer readable storage medium may be any tangible medium that can contain, or store a program for use by or in connection with an instruction execution system, apparatus, or device.

An input/output circuit 1160 may include displays and/or user input devices, such as keyboards, touch screens and/or pointing devices. Devices attached to the input/output circuit 1160 may be used to provide information to the processor 1140 by a user of the classification system 1100. Devices attached to the input/output circuit 1160 may include networking or communication controllers, input devices (keyboard, a mouse, touch screen, etc.) and output devices (printer or display). The input/output circuit 1160 may also provide an interface to devices, such as a display and/or printer, to which results of the operations of the classification system 1100 can be communicated so as to be provided to the user of the classification system 1100.

An optional update circuit 1180 may be included as an interface for providing updates to the classification system 1100. Updates may include updates to the code executed by the processor 1140 that are stored in the memory 1150 and/or the storage circuit 1170. Updates provided via the update circuit 1180 may also include updates to portions of the storage circuit 1170 related to a database and/or other data storage format which maintains information for the classification system 1100, such as the signatures (i.e., pre-determined sets of genes), weights, thresholds, etc.

The sample input circuit 1110 of the classification system 1100 may provide an interface for the platform as described hereinabove to receive biological samples to be analyzed. The sample input circuit 1110 may include mechanical elements, as well as electrical elements, which receive a biological sample provided by a user to the classification system 1100 and transport the biological sample within the classification system 1100 and/or platform to be processed. The sample input circuit 1110 may include a bar code reader that identifies a bar-coded container for identification of the sample and/or test order form. The sample processing circuit 1120 may further process the biological sample within the classification system 1100 and/or platform so as to prepare the biological sample for automated analysis. The sample analysis circuit 1130 may automatically analyze the processed biological sample. The sample analysis circuit 1130 may be used in measuring, e.g., gene expression levels of a pre-defined set of genes with the biological sample provided to the classification system 1100. The sample analysis circuit 1130 may also generate normalized gene expression values by normalizing the gene expression levels. The sample analysis circuit 1130 may retrieve from the storage circuit 1170 a pre-defined weighting values (i.e., coefficients) for each of the genes of the pre-defined set of genes. The sample analysis circuit 1130 may enter the normalized gene expression values. The sample analysis circuit 1130 may calculate an etiology probability for sepsis based upon the weighted normalized gene expression values, via the input/output circuit 1160.

The sample input circuit 1110, the sample processing circuit 1120, the sample analysis circuit 1130, the input/output circuit 1160, the storage circuit 1170, and/or the update circuit 1180 may execute at least partially under the control of the one or more processors 1140 of the classification system 1100. As used herein, executing "under the control" of the processor 1140 means that the operations performed by the sample input circuit 1110, the sample processing circuit 1120, the sample analysis circuit 1130, the input/output circuit 1160, the storage circuit 1170, and/or the update circuit 1180 may be at least partially executed and/or directed by the processor 1140, but does not preclude at least a portion of the operations of those components being separately electrically or mechanically automated. The processor 1140 may control the operations of the classification system 1100, as described herein, via the execution of computer program code.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the classification system 1100, partly on the classification system 1100, as a stand-alone software package, partly on the classification system 1100 and partly on a remote computer or entirely on the remote computer or server. In the latter scenario, the remote computer may be connected to the classification system 1100 through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

In some embodiments, the system includes computer readable code that can transform quantitative, or semi-quantitative, detection of gene expression to a cumulative score or probability of sepsis.

In some embodiments, the system is a sample-to-result system, with the components integrated such that a user can simply insert a biological sample to be tested, and some time later (preferably a short amount of time, e.g., 15, 30 or 45 minutes, or 1, 2, or 3 hours, up to 8, 12, 24 or 48 hours) receive a result output from the system.

It is to be understood that the invention is not limited in its application to the details of construction and the arrangement of components set forth in the following description or illustrated in the following drawings. The invention is capable of other embodiments and of being practiced or of being carried out in various ways.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following examples are illustrative only and are not intended to be limiting in scope.

EXAMPLES

Example 1. Mortality Prediction in Sepsis Via Gene Expression Analysis: A Community Approach Improved risk stratification and prognosis in sepsis is a critical unmet need. Clinical severity scores and available assays such as blood lactate reflect global illness severity with suboptimal performance, and do not specifically reveal the underlying dysregulation of sepsis. Here, three scientific groups were invited to independently generate prognostic models for 30-day mortality using 12 discovery cohorts (N=650) containing transcriptomic data collected from primarily community-onset sepsis patients. Predictive performance was validated in 5 cohorts of community-onset sepsis patients (N=189) in which the models showed summary AUROCs ranging from 0.765-0.89. Similar performance was observed in 4 cohorts of hospital-acquired sepsis (N=282). Combining the new gene-expression-based prognostic models with prior clinical severity scores led to significant improvement in prediction of 30-day mortality (p<0.01). These models provide an opportunity to develop molecular bedside tests that may improve risk stratification and mortality prediction in patients with sepsis, improving both resource allocation and prognostic enrichment in clinical trials.

Methods

Systematic Search. Two public gene expression repositories (NCBI GEO[24], EMBL-EBI ArrayExpress[25]) were searched for all clinical gene expression microarray or next-generation sequencing (NGS/RNAseq) datasets that matched any of the following search terms: sepsis, SIRS, trauma, shock, surgery, infection, pneumonia, critical, ICU, inflammatory, nosocomial. Clinical studies of acute infection and/or sepsis using whole blood were retained. Datasets that utilized endotoxin or LPS infusion as a model for inflammation or sepsis were excluded. Datasets derived from in sorted cells (e.g., monocytes, neutrophils) were also excluded.

Overall, 16 studies containing 17 different cohorts were included (Table 1a-b). These 16 studies include expression profiles from both adult[13,15,17,26-35] and pediatric[31,36-39] cohorts. In these cases, the gene expression data were publicly available. When mortality and severity phenotypes were unavailable in the public data, the data contributors were contacted for this information. This included datasets E-MTAB-1548[11,40], GSE10474[27], GSE21802[33], GSE32707[30], GSE33341[34], GSE63042[17], GSE63990[35], GSE66099[39], and GSE66890[32]. Furthermore, where longitudinal data was available for patients admitted with sepsis, we only included data derived from the first 48 hours after admission. The E-MTAB-4421 and E-MTAB-4451 cohorts both came from the GAinS study[13], used the same inclusion/exclusion criteria, and were processed on the same microarray type. Thus, after re-normalizing from raw data, we used ComBat normalization[41] to co-normalize these two cohorts into a single cohort, which we refer to as E-MTAB-4421.51. In addition to the above 17 datasets, we identified four additional privately-held datasets (Table 1c) representing patients with HAI. In-depth summaries of each HAI cohort can be found in the supplementary text.

TABLE 1

Datasets included in the analysis.

| Accession | Ref # | First Author | Cohort Description | Timing of sepsis diagnosis | Age | Sex (% male) | Severity | Country | N Survived | N Died |
|---|---|---|---|---|---|---|---|---|---|---|
| *1a: Discovery Cohorts* | | | | | | | | | | |
| E-MEXP-3567 | 32 | Irwin | Children with meningococcal sepsis +/− HIV co-infection | Admission to ED | 2.0 (IQR 0.6-6.9) | 55 | unk. | Malawi | 6 | 6 |
| E-MEXP-3850 | 33, 34 | Kwan | Children w/ meningococcal sepsis | Admission to hospital; sampled at multiple times 0-48 hrs | 1.3 (range 0.8-2.0) | 40 | PELOD; 29.2 (range 11-61) | UK | 19 | 5 |
| E-MTAB-1548 | 13, 36 | Almansa | Adults with sepsis after surgery (EXPRESS study) | Average post-operation day 4 (hospital acquired) | 69.7 (std. dev. 13.1) | 67 | APACHE II 17.0 (std. dev. 5.4) | Spain | 50 | 24 |
| GSE10474 | 23 | Howrylak | Adults in MICU with sepsis +/− acute lung injury | Admission to ICU | 57 (std. dev. 4.3) | 45 | APACHE II 20.7 (std. dev. 1.6) | USA | 22 | 11 |
| GSE13015a GSE13015b | 23, 24 | Pankla | Adults with sepsis, many from burkholderia | Within 48 hours of diagnosis; both community-acquired and hospital-acquired. | 54.7 (std. dev. 11.7) | 54 | unk. | Thailand | 35 8 | 13 7 |
| G5E27131 | 25 | Berdal | Adults with severe H1N1 influenza requiring mechanical ventilation | Admission to ICU | unk. | unk. | SAPS II 29.3 (std.dev. 10.3) | Norway | 5 | 2 |
| G5E32707 | 55 | Dolinay | Adults in MICU with sepsis +/− ARDS | Admission to ICU | 57.1 (std. dev. 14.9) | 53 | APACHE II 26.7 (std. dev. 8.5) | USA | 31 | 17 |
| GSE40586 | 27 | Lill | Infants, children, and adults with bacterial meningitis | Within 48 hours of hospital admission | 43.4 (range 17 days - 70 years) | unk. | unk. | Estonia | 19 | 2 |
| GSE63042 | 12 | Tsalik | Adults with sepsis (CAPSOD study) | Admission to ED | 59.1 (std. dev. 18.3) | 59 | APACHE II 16.5 (std. dev. 7.3) | USA | 76 | 28 |
| GSE66099 | 35 | Wong | Children in ICU with sepsis/septic shock | Admission to ICU | 3.7 | 58 | PRISM 15.7 | USA | 171 | 28 |
| GSE66890 | 28 | Kangelaris | Adults in ICU with sepsis +/− ARDS | Admission to ICU | 63 (std. dev 19) | 56 | APACHE III 100 (std. dev. 35) | USA | 43 | 14 |
| *1b: Validation Cohorts* | | | | | | | | | | |
| GSE21802 | 29 | Bermejo-Martin | Adults in ICU with severe H1N1 influenza | Within 48 hours of admission to ICU | 43 (std. dev. 11) | 47 | SOFA 4.1 (std. dev. 3.5) | Spain | 7 | 4 |
| GSE33341 | 30 | Ahn | Adults with 2+ SIRS criteria and bacteremia | Within 24 hours of admission to hospital | 58 (range 24-91) | 61 | unk. | USA | 49 | 2 |
| GSE54514 | 10 | Parnell | Adults in ICU with sepsis | Admission to ICU | 61 (std. dev. 16) | 40 | APACHE II 21 (std. dev. 6) | Australia | 26 | 9 |
| G5E63990 | 31 | Tsalik | Adults with bacterial infection plus 2+ SIRS criteria | Admission to ED | 49 (range 14-88) | 50 | unk. | USA | 64 | 6 |
| E-MTAB-4421.51 | 15 | Davenport | Adults with sepsis (GAinS study) | Within 24 hours of admission to ICU | 64.2 (std. dev. 15.2) | 55 | APACHE II 18.6 (std. dev. 9.7) | UK | 15 | 7 |
| *1c: Hospital-Acquired Infection Cohorts* | | | | | | | | | | |
| Duke HAI | none | Tsalik (unpublished) | Adults who developed HAI, some VAP | Hospital days 1-30 | 58.0 (std. dev. 17.9) | 75 | unk. | USA | 60 | 10 |
| Glue Grant | needed | Glue Grant | Adults with severe burns (whole blood) | Hospital days 1-30 | 14.1 (std. dev. 16.2) | 64 | Denver Score 1.5 | USA | 84 | 8 |

TABLE 1-continued

Datasets included in the analysis.

| Accession | Ref # | First Author | Cohort Description | Timing of sepsis diagnosis | Age | Sex (% male) | Severity | Country | N Survived | N Died |
|---|---|---|---|---|---|---|---|---|---|---|
| Burns Glue Grant Trauma | needed | authors Glue Grant authors | Adults with severe traumatic injuries (buffy coat) | Hospital days 1-30 | 33.2 (std. dev. 10.2) | 74 | (std. dev. 1.7) MODS 6.4 (std. dev. 3.3) | USA | 48 | 1 |
| UF P50 12H | none | Moldawer (unpublished) | Adults with hospital-acquired sepsis | Hospital days 1-30 | unk. | unk. | SOFA 5.5 (std. dev. 3.9) | USA | 66 | 5 |

Unk, unknown data or not available;
IQR, inter-quartile range;
std. dev., standard deviation;
ED, emergency department;
ICU, intensive care unit;
MICU, medical
ICU; ARDS, acute respiratory distress syndrome;
SIRS, systemic inflammatory response syndrome;
VAP, ventilator-associated pneumonia.

We selected cohorts as either discovery or validation based on their availability. Studies for which outcome data was readily available were included as discovery cohorts. Only GSE54514[15] was initially held out for validation given its large size and representative patient characteristics. After we had trained the models some outcomes data became newly available, so so these were added as validation cohorts[13,33-35]. Additionally, given the known differences in sepsis pathophysiology and gene expression profiles as compared to patients with community-acquired sepsis[39,42], the HAI datasets were set aside as a second validation cohort. The validation cohorts were not matched to the discovery cohort on any particular criteria but rather provide a validation opportunity across a heterogeneous range of clinical scenarios.

Gene Expression Normalization. All Affymetrix datasets were downloaded as CEL files and re-normalized using the gcRMA method (R package affy[43]). Output from other array types were normal-exponential background corrected and then between-arrays quantile normalized (R package limma[44]). For all gene analyses, the mean of probes for common genes was set as the gene expression level. All probe-to-gene mappings were downloaded from GEO from the most current SOFT files.

Two of the cohorts, CAPSOD[17] and the Duke HAI cohort, were assayed via NGS. For compatibility with micro-array studies, expression from NGS data sets were downloaded as counts per million total reads (CPM) and were normalized using a weighted linear regression model using the voom method[45] (R package limma[44]). The estimated precision weights of each observation were then multiplied with the corresponding log 2(CPM) to yield final gene expression values.

Prediction Models. Prediction models were built by comparing patients who died within 30 days of hospital admission with sepsis to patients who did not. In the CAPSOD dataset (which was used in model training) we excluded two patients with unclear mortality outcomes, and one patient who died in-hospital but after 30 days. Mortality was modeled as a binary variable as since time-to-event data were not available. Overall, a total of four prognostic models were built by three different academic groups (Duke University, Sage Bionetworks, and Stanford University). All four models started with the same gene expression data in the discovery phase. Each model was built in two phases: a feature selection phase based on statistical thresholds for differential gene expression across all discovery cohorts, and then a model construction phase optimizing classification power. Full descriptions of the four models can be found in the supplementary text of Example 2 below, and in FIG. 3-FIG. 5.

Comparison with severity scores. We compared the prognostic accuracy of the gene scores with the prognostic accuracy of clinical severity scores (APACHE II, PELOD, PRISM, SAPS II, SOFA, and the Denver score) where such information was available. These clinical severity scores were not necessarily built to predict mortality in the specific populations in which they were used here, but nonetheless serve as important comparators for the gene expression models. To compare prognostic power, logistic regression was performed to predict mortality using either the clinical severity score or the given gene model's output score. We then tested a combined model (mortality as a function of clinical severity and gene score, without interaction term) and measured the AUROC of the combined model. Comparisons were made between AUROCs with paired t-tests.

Discriminatory Power Analyses. We examined class discriminatory power for separating survivors from non-survivors using receiver operating characteristic (ROC) curves of the gene scores within datasets. The area under the ROC curves (AUROC) was calculated using the trapezoidal method. Summary ROC curves were calculated via the method of Kester and Buntinx[46,47]. We examined the ability of the models to predict non-survivors using precision-recall curves generated from the gene scores in each examined dataset. Precision-recall curves of the gene scores were constructed within datasets, and the area under the precision-recall curve (AUPRC) was calculated using the trapezoidal method.

Enrichment Analysis. We conducted two analyses to evaluate the functional enrichment of the genes selected as predictors by the four models. This included a targeted enrichment analysis for cell types as previously described[39] and an exploratory enrichment analysis that assessed a large number of functionally annotated gene sets.

In a mixed tissue such as blood, shifts in gene expression can be caused by changes in cell type distribution. To check for this effect, we used gene expression profiles derived from known sorted cell types to determine whether a given set of genes is enriched for genes represented in a specific cell type. In each curated cell type vector, a 'score' is calculated by the geometric mean of the upregulated genes minus the geometric mean of the downregulated genes. A higher 'score' represents a greater presence of the given cell type in the differential gene expression signature.

For exploratory enrichment, we curated thousands of gene sets from two widely-used databases: gene ontology (GO)[48] and the Reactome database of pathways and reactions in human biology[49,50]. Our 12 discovery cohorts had approximately 6,000 genes in common, which formed a 'background' set of genes. We removed all genes not in the background genes from the Reactome/GO sets. We then retained all Reactome/GO gene sets containing at least 10% and at least 3 genes overlapping with the predictor genes. The remaining Reactome/GO gene sets were removed to reduce the multiple testing burden. Fisher's Exact test was used to test enrichment in each of the curated reference gene sets. Both nominal and Benjamini-Hochberg-corrected significance were tested.

Statistics. All computation and calculations were carried out in the R language for statistical computing (version 3.2.0) and Matlab R 2016a (The MathWorks, Inc.). Significance levels for p-values were set at 0.05 and analyses were two-tailed.

Results

Analysis Overview. We used a community approach to build gene-expression-based models predictive of sepsis-induced mortality using all available gene expression datasets (21 total cohorts, Table 1). In this community approach, three different teams (Duke University, Sage Bionetworks, and Stanford University) performed separate analyses using the same input data; we thus sampled the possible model space to determine whether output performance is a function of analytical approaches (FIG. 1). Two models (Duke and Stanford) used parameter-free difference-of-means formulae for integrating gene expression, and the other two models (both from Sage Bionetworks) used penalized logistic regression (LR)[51] and random forests (RF)[52].

Each of the four models was trained using 12 discovery cohorts (485 survivors and 157 non-survivors) composed primarily of patients with community-acquired sepsis. Performance was evaluated across two groups of heterogeneous validation data sets (5 community-acquired sepsis cohorts with 161 survivors and 28 non-survivors and 4 HAI cohorts with 258 survivors and 24 non-survivors, Table 1). The community-acquired sepsis and HAI cohorts were considered separately in validation because of their known differences in host-response profiles. Due to the nature of public datasets, we had limited information on demographics, infection, severity and treatment and so these variables were not controlled for in model selection. The cohorts included patients from multiple age groups, countries, and hospital wards (emergency department, hospital ward, medical ICU, and surgical ICU). As expected in varied patient populations, mortality rates varied widely across cohorts (mean 23.2%±13.4%).

Figure 2:
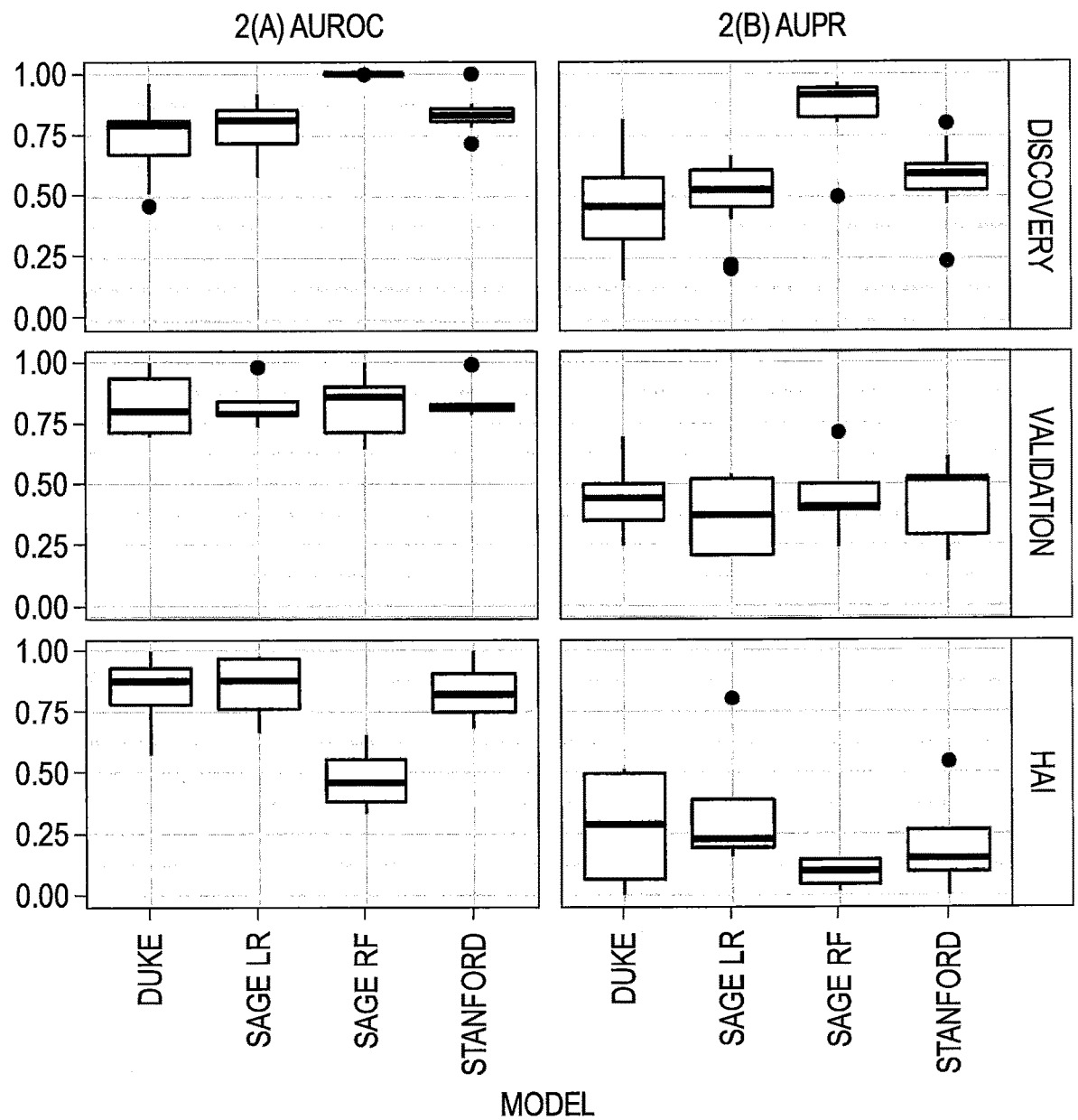
FIG. 2 is a graph showing model performance in accordance with one embodiment of the present disclosure.
Figure 6:
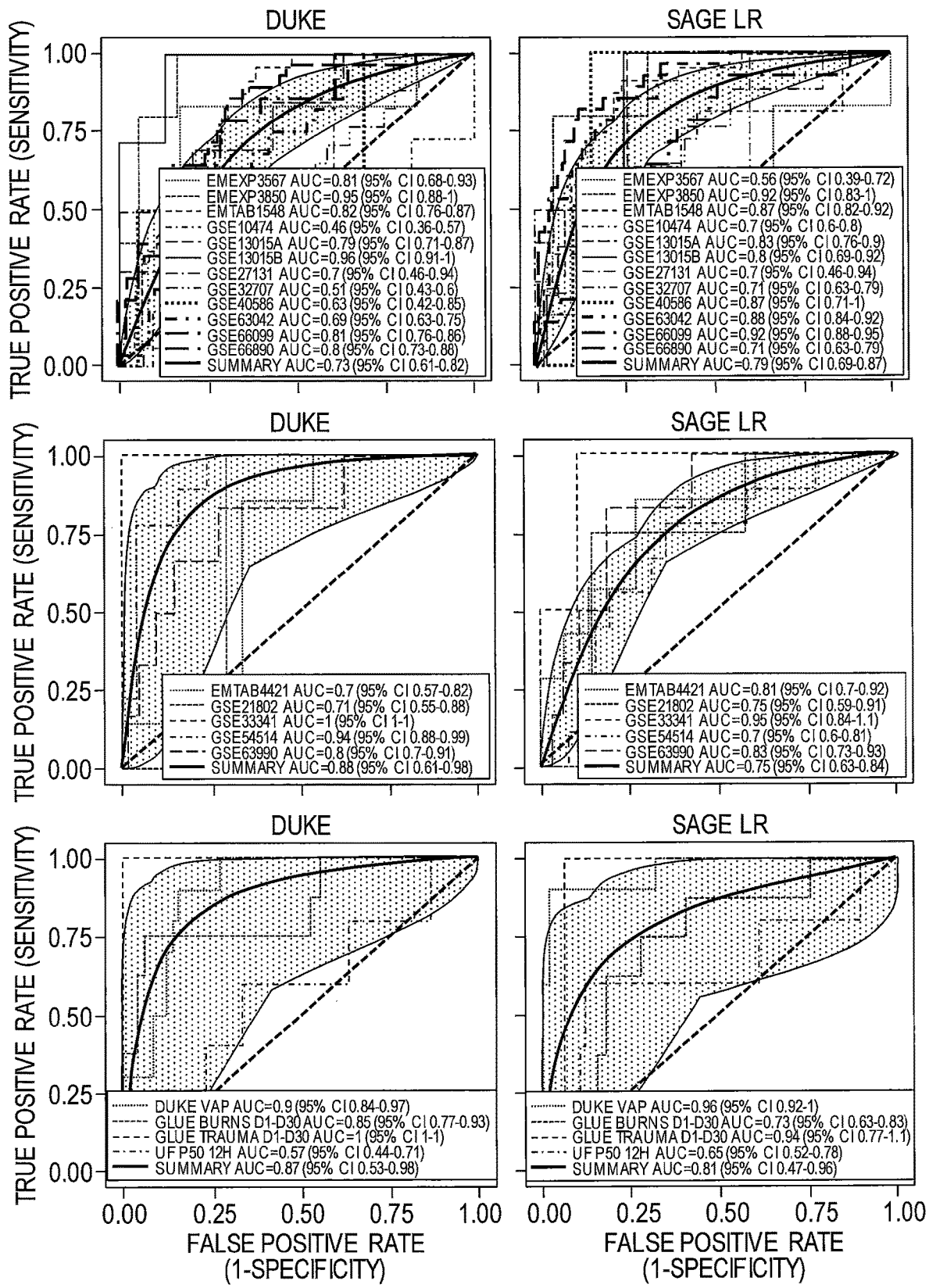
FIG. 6 presents model performance showing individual ROC curves and summary ROC curve with confidence intervals (black and grey).
Figure 6:
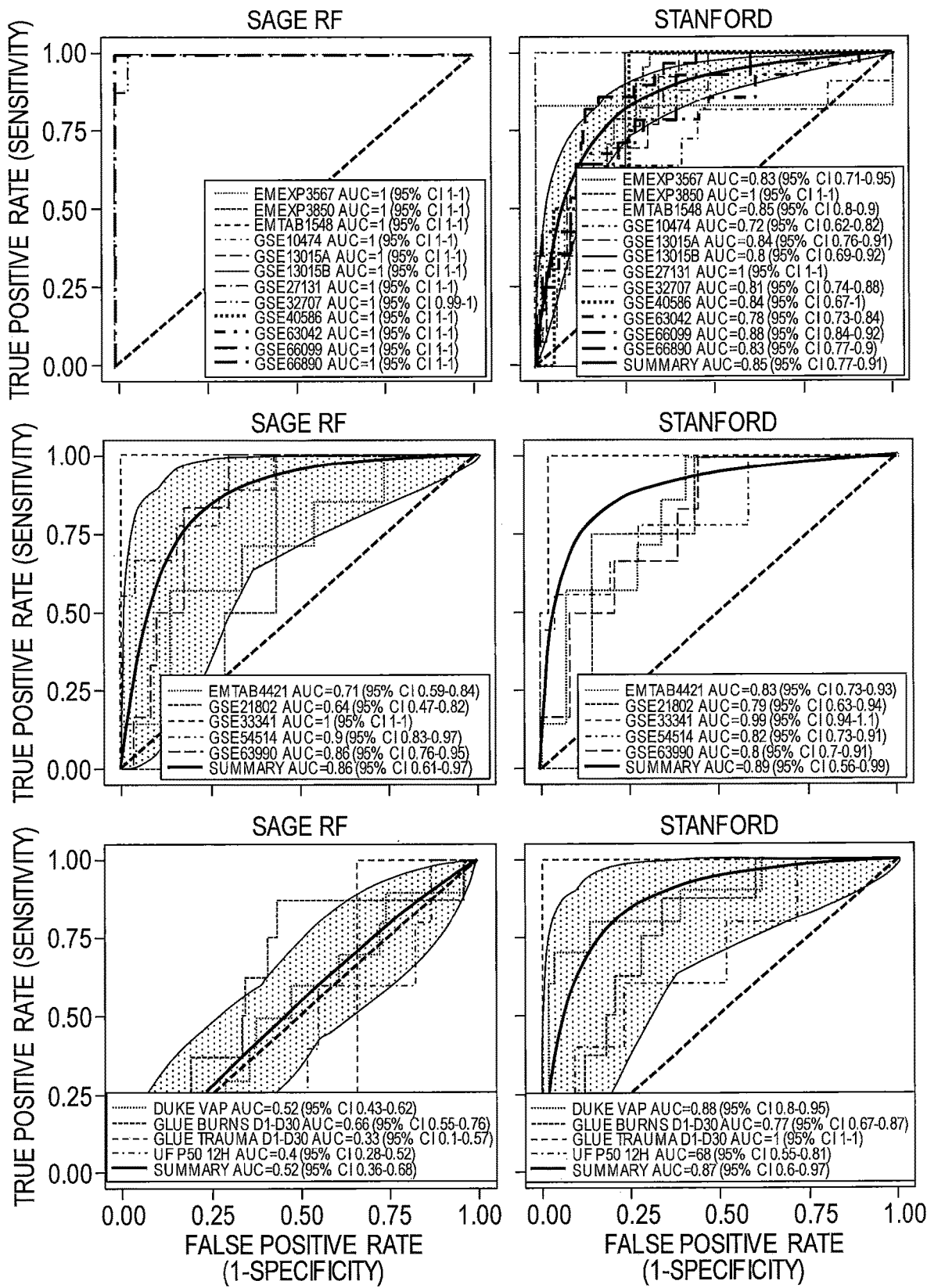
Figure 7:
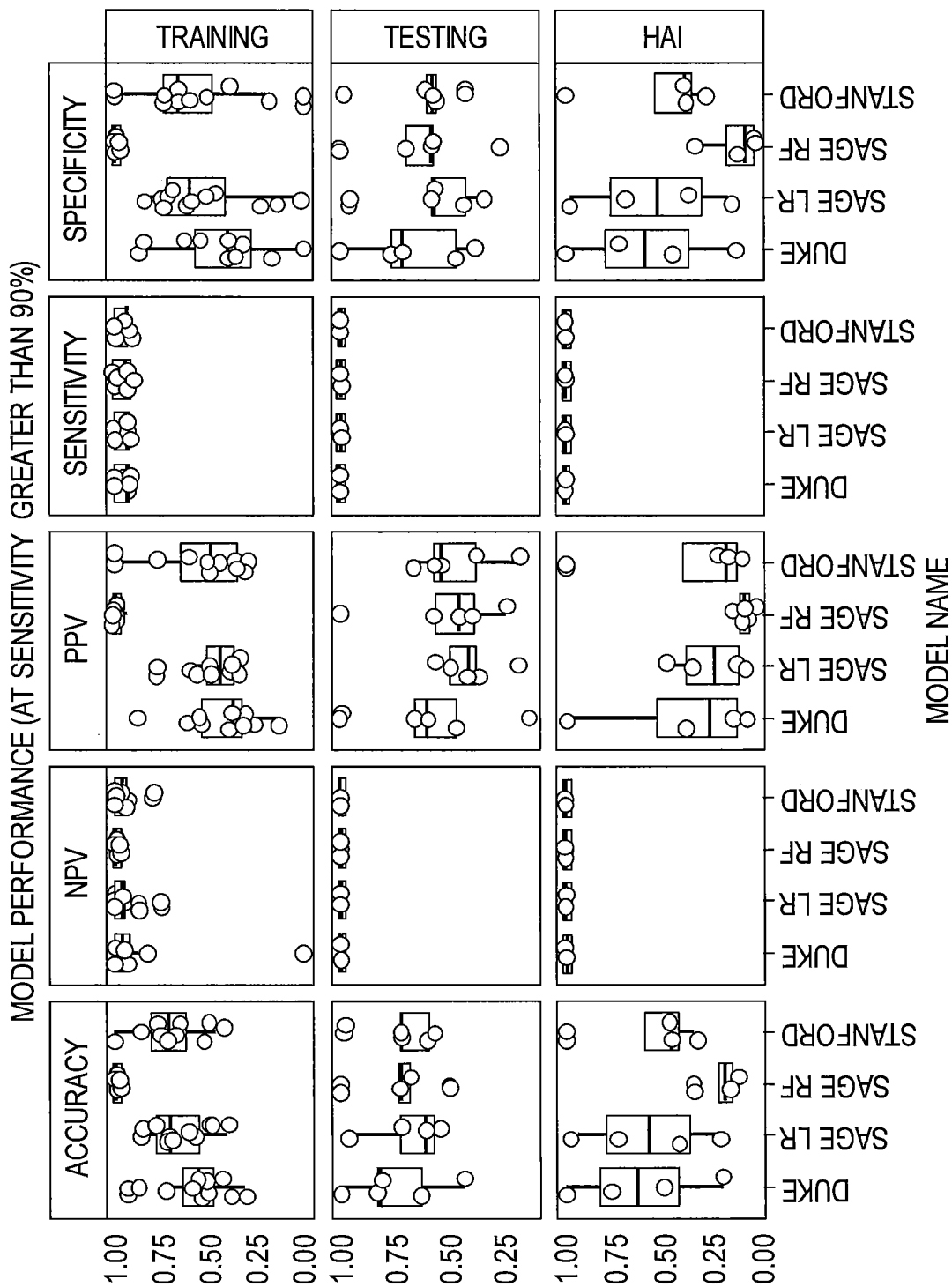
FIG. 7 provides boxplots of other performance metrics for each model in individual cohorts, with cutoffs set to the sensitivity nearest to 90%.

Prognostic Power Assessments. Model performance was primarily evaluated using ROC analysis separately in the discovery, validation, and HAI cohorts. Boxplots of the AUROCs for each model are shown in FIG. 2; data from individual cohorts and summary ROC curves are shown in Supplementary Tables 1-2 and FIG. 6. Across the five community-acquired sepsis validation datasets, the four models showed generally preserved prognostic power, with summary AUROCs ranging from 0.75 (95% CI 0.63-0.84, Sage LR) to 0.89 (95% CI 0.56-0.99, Stanford). Three of the four models performed well in classifying the HAI datasets (summary AUROCs 0.81-0.87 in the Duke, Sage LR, and Stanford models); one model performed poorly in HAI (summary AUROC 0.52, 95% CI 0.36-0.68, Sage RF). Overall, most models performed equivalently in discovery, validation, and HAI datasets. To judge other performance metrics including accuracy, specificity, NPV and PPV, we set thresholds for each model at the nearest sensitivity >90% (FIG. 7).

To assess whether the models contained complementary orthogonal information, we evaluated the prediction accuracy of an ensemble model based on the predictions of all four individual models. The prognostic power of the ensemble model was at an average AUROC of 0.81 across all five validation data sets (paired t-tests vs. individual models all p=NS, Supplementary Table 3) indicating that the present diagnostic accuracy may be a rough estimate of the ceiling of prognostic accuracy inherent in these data.

Performance in predicting non-survivors was evaluated using the area under the precision-recall curve (AUPRC) (FIG. 2, right side (2(b)) & Supplementary Table 4). The AUPRCs for non-survivor prediction were notably lower than the AUROCs, suggesting that the models' primary utility may be in ruling out mortality for individuals much less likely to die within 30 days as opposed to accurately identifying the minority of patients who are highly likely to die within 30 days. On the contrary the AUPRC of the ensemble model was averaged at 0.428 in validation cohorts (Supplementary Table 3), suggesting complementarity in discriminatory power between individual models.

Comparison to Standard Predictors. We next assessed whether the performance of these gene expression-based predictors of mortality outperformed standard clinical severity scores. Notably, clinical measures of severity were only available in a subset of cohorts (8 discovery, 3 validation, 3 HAI; Supplemental Table 5). The mean differences in gene model over clinical severity scores were: Duke −0.044; Sage LR 0.010; Sage RF 0.094; Stanford 0.064; only the Stanford model trended towards significance (paired t-test p=0.098). However, we combined gene models and clinical severity scores into joint predictors, and each combination significantly outperformed clinical severity scores alone (all paired t-tests p≤0.01). This suggests that the gene expression-based predictors add significant prognostic utility to standard clinical metrics.

Figure 8:
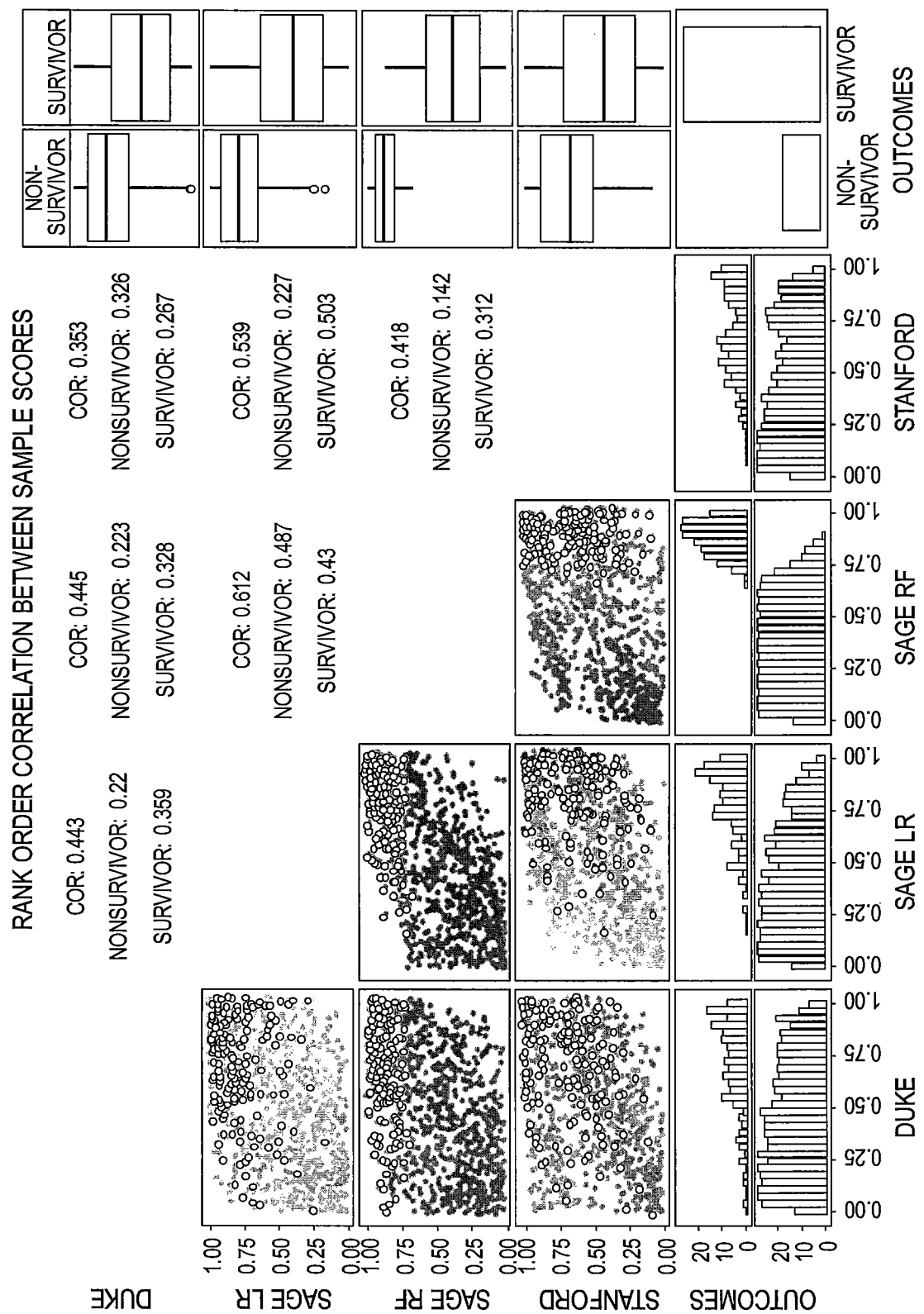
FIG. 8 presents graphs showing the rank order correlation between sample scores across the four models for all samples.

Comparison Across Models. We next studied whether models were correctly classifying the same patients or whether each model was correctly classifying different groups of patients. We tested model correlations across all patients by comparing the relative ranks of each patient within each model instead of comparing raw model scores. We found the models were moderately correlated (Spearman rho=0.35-0.61, FIG. 8). We then evaluated the agreement between the four models by comparing model-specific patient classifications (Supplementary Table 6). For this purpose, we chose cutoffs for each model that yielded 90% sensitivities for non-survivors. We then labeled patients as being either always misclassified, correctly classified by 1 or 2 models (no consensus), or correctly classified in at least 3 of 4 models (consensus). As expected by the 90% sensitivity threshold, 10% of patients were misclassified by all models. In the remaining cases, 63% were correctly predicted by consensus and 27% do not reach consensus. Together, the model correlation and consensus analyses showed that 73% of patients were classified with consensus among different models, with variance leading to discordance in the remaining 27%.

Biology of the Gene Signatures of Mortality. Gene predictors were chosen for both optimized prognostic power and sparsity in our data-driven approach and so do not necessarily represent key nodes in the pathophysiology of sepsis. Still, we examined whether interesting biology was being represented in the models. We first looked for overlap in the gene sets used for prediction across the four models, but found few genes in common (Table 2). Since each signature had too few genes for robust analysis, we analyzed the genes from all four models in aggregate, resulting in 58 total genes (31 up-regulated and 27 down-regulated, Supplementary Table 7).

TABLE 2

Genomic predictors of sepsis mortality

| Model Name | Direction | Genomic Features |
|---|---|---|
| Duke | Up Regulated (5 genes) | TRIB1, CKS2, MKI67, POLD3, PLK1 |
| | Down regulated (13 genes) | TGFBI, LY86, CST3, CBFA2T3, RCBTB2, TST, CX3CR1, CD5, MTMR11, CLEC10A, EMR3, DHRS7B, CEACAM8 |
| Sage LR | Up regulated (9 genes) | CFD, DDIT4, DEFA4, IFI27, IL1R2, IL8, MAFF, OCLN, RGS1 |
| | Down regulated (9 genes) | AIM2, APH1A, CCR2, EIF5A, GSTM1, HIST1H3H, NT5E, RAB40B, VNN3 |
| Sage RF | Up regulated (13 genes) | B4GALT4, BPI, CD24, CEP55, CTSG, DDIT4, G0S2, MPO, MT1G, NDUFV2, PAM, PSMA6, SEPP1 |
| | Down Regulated (4 genes) | ABCB4, CTSS, IKZF2, NT5E |
| Stanford | Up regulated (8 genes) | DEFA4, CD163, PER1, RGS1, HIF1A, SEPP1, C11orf74, CIT |
| | Down Regulated (4 genes) | LY86, TST, OR52R1, KCNJ2 |

Figure 9:
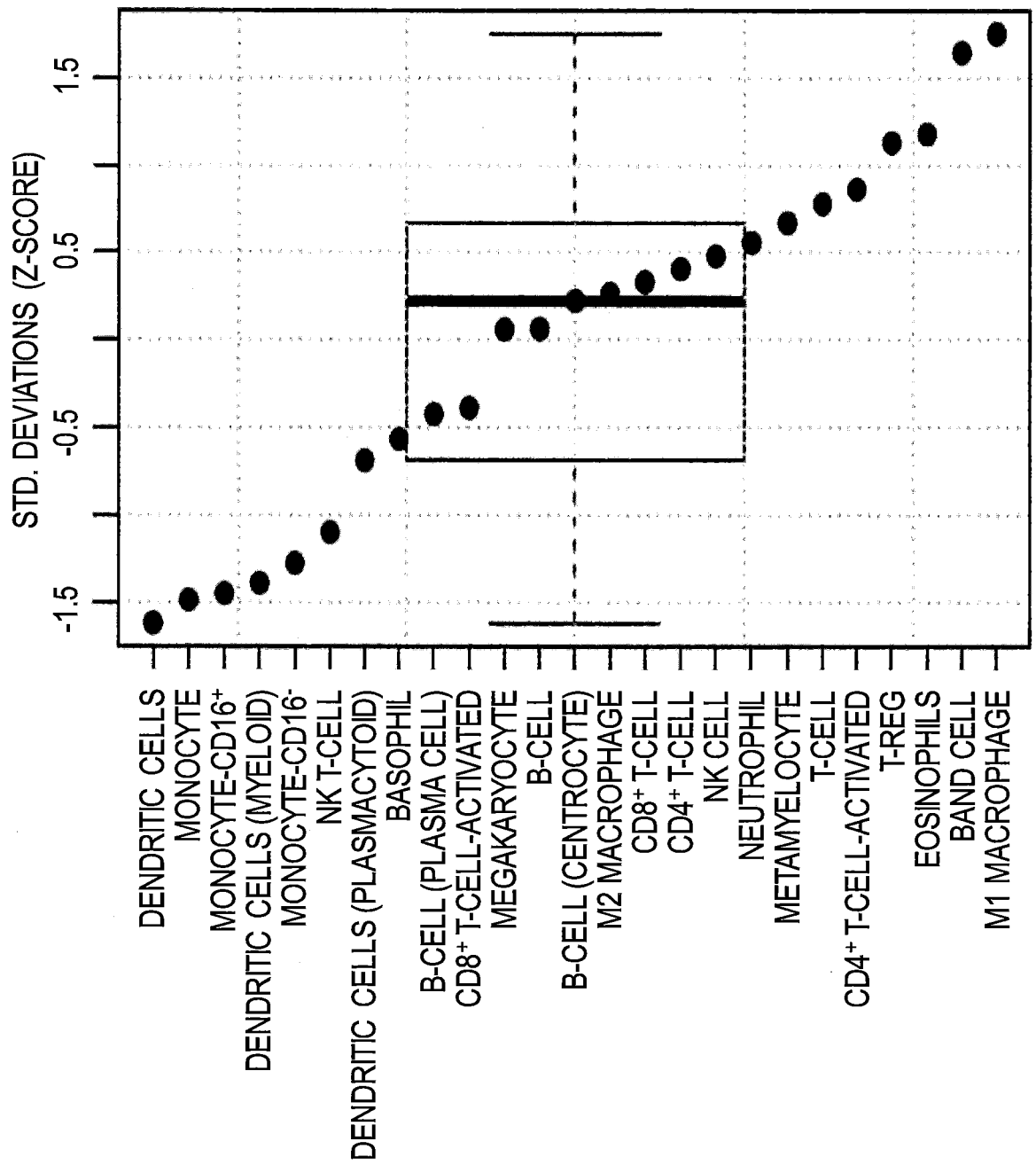
FIG. 9 is a graph showing cell type enrichments of the entire set of 58 genes used across all four prediction models.

First, we studied whether the differential gene expression identified may be indicative of cell-type shifts in the blood. The pooled gene sets were tested in several known in vitro gene expression profiles of sorted cell types to assess whether gene expression changes are due to cell type enrichment (FIG. 9). No significant differences were found, but the trend showed an enrichment of M1-polarized macrophages and band cells (immature neutrophils), and under-expression in dendritic cells. This is consistent with a heightened pro-inflammatory response and a decrease in adaptive immunity in patients who ultimately progress to mortality[10].

We next tested the 58 genes for enrichment in gene ontologies and Reactome pathways, but after multiple hypothesis testing corrections, no pathways were significantly enriched. This may be either due to the relatively low number of genes in the predictor set, or it may indicate that there is not unified biology across the four models. In addition, the models were generated in a way that penalized the inclusion of genes that were redundant for classification purposes. However, since genes redundant for classification purposes are often from the same biological pathway, their exclusion from the models limits the utility of enrichment analyses. Pathways at a nominal enrichment (p value<=0.05) are shown in Supplementary Table 8. A brief examination of pathways marginally activated in non-survivors showed cell division, apoptosis, hypoxia, and metabolic networks. Pathways marginally activated in survivors included pro-inflammatory and metabolic networks.

Discussion

Sepsis is a heterogeneous disease, including a wide possible range of patient conditions, pre-existing comorbidities, severity levels, infection incubation times, and underlying immune states. Many investigators have hypothesized that molecular profiling of the host response may better predict sepsis outcomes. Here, we extensively assessed the predictive performance of whole-blood gene expression using a community-based modeling approach. This approach was designed to evaluate predictive capabilities in a manner that was independent of specific methodological preferences, and instead created robust prognostic models across a broad solution space. We developed four state-of-the-art data-driven prognostic models using a comprehensive survey of available data including 21 different sepsis cohorts (both community-acquired and hospital-acquired, N=1,113 patients), with summary AUROCs around 0.85 for predicting 30-day mortality. We also showed that combining the gene-expression-based models with clinical severity scores leads to significant improvement in the ability to predict 30-day mortality, indicating clinical utility.

Prediction of outcomes up to 30 days after the time of sampling represents a difficult task, given that the models must account for all interventions that occur as part of the disease course. An accuracy of 100% is likely not only not achievable but also not desirable, as it would suggest that mortality is pre-determined and independent of clinical care. Given this background, and since similar prognostic power was observed across all individual models and the ensemble model, our prognostic accuracy may represent an upper bound on transcriptomic-based prediction of sepsis outcomes. In addition, since prognostic accuracy was retained across broad clinical phenotypes (children and adults, with bacterial and viral sepsis, with community-acquired and hospital-acquired infections, from multiple institutions around the world) the models appear to have successfully incorporated the broad clinical heterogeneity of sepsis.

Sepsis remains difficult to define. The most recent definition of sepsis (Sepsis-3) requires the presence organ dysfunction as measured by an increase in SOFA of two or more points over baseline[1]. Determining the SOFA score can help guide which organ systems are dysfunctional, but this fails to characterize the biological changes are driving the septic response. Molecular tools like the ones developed here provide an opportunity to provide a simple, informative prognosis for sepsis by improving patient risk stratification. Host response profiles could also help to classify patients with sepsis as opposed to non-septic acute infections. Identifying such high-risk patients may also lead to greater success in clinical trials through improved enrichment strategies. This identification of subgroups or 'endotypes' of sepsis has already been successfully applied to both pediatric and adult sepsis populations[12,13].

The goal of this study was to generate predictive models but not necessarily to define sepsis pathophysiology. However, our community approach identified a large number of genes associated with sepsis mortality that may point to underlying biology. The association with immature neutrophils and inflammation in sepsis has been previously shown[53]. Results of this study confirm this finding as we note increases in the neutrophil chemoattractant IL-8 as well as neutrophil-related antimicrobial proteins (DEFA4, BPI, CTSG, MPO). These azurophilic granule proteases may indicate the presence of very immature neutrophils (metamyelocytes) in the blood[54]. Many of these genes have also been noted in the activation of neutrophil extracellular traps (NETs)[55,56]. NET activation leads to NETosis, a form of neutrophil cell death that can harm the host[56]. Whether these involved genes are themselves harmful or are markers of a broader pathway is unknown. Along with immune-related changes, there are changes in genes related to hypoxia and energy metabolism (HIF1A, NDUFV2, TRIB1). Of particular interest is the increase in HIF1A, a hypoxia-induced transcription factor. This may be evidence of either a worsening cytopathic hypoxia in septic patients who progress to mortality, or of a shift away from oxidative metabolism ("pseudo-Warburg" effect), or both[57]. Modification of the Warburg effect due to sepsis has been implicated in immune activation[58,59], trained immunity[60], and immunoparalysis[61].

The present study has several limitations. First, as a retrospective study of primarily publically available data, we are not able to control for demographics, infection, patient severity, or individual treatment. However, our successful representation of this heterogeneity likely contributed to the successful validation in external community-acquired and hospital-acquired sepsis cohorts. Second, despite a large amount of validation data, we do not present the results of any prospective clinical studies of these biomarkers. Prospective analysis will be paramount in translating the test to a clinically relevant assay. Third, the genes identified here were specifically chosen for their performance as biomarkers, not based on known relevance to the underlying pathophysiology of mortality in sepsis. As such, the biological insights gained from these biomarkers will need to be confirmed and expanded on by studies focused on the entire perturbation of the transcriptome during sepsis and through targeted study of individual genes and pathways. Fourth, the use of 30-day mortality as our endpoint is a crude measure of severity, and may miss important intermediate endpoints such as prolonged ICU stay or poor functional recovery. While such intermediate outcomes were not available in the current data, the models' abilities to predict these functional outcomes will need to be tested prospectively.

Researchers, clinicians, funding agencies, and the public are all advocating for improved platforms and policies that encourage sharing of clinical trial data[62]. Meta-analysis of multiple studies leads to results that are more reproducible than from similarly-powered individual cohorts. The community approach used here has shown that aggregated transcriptomic data can be used to define novel prognostic models in sepsis. This collaboration of multidisciplinary teams of experts encompassed both analytical and statistical rigor along with deep understandings of both the transcriptomics data and clinical data. When more data becomes available, such as demographics, treatments, clinical outcomes, other data types like proteomics and metabolomics, then the model can be improved. Data-driven collaborative modelling approaches using these data can be effective in discovering new clinical tools.

Conclusions

We have shown comprehensively that patients with acute infections can be risk-stratified based on their gene expression profiles at the time of diagnosis. The overall performance of expression-based predictors paired with clinical severity scores was significantly higher than clinical scores alone. These gene expression models reflect a patient's underlying biological response state and could potentially serve as a valuable clinical assay for prognosis and for defining the host dysfunction responsible for sepsis. These results serve as a benchmark for future prognostic model development and as a rich source of information that can be mined for additional insights. Improved methods for risk stratification would allow for better resource allocation in hospitals and for prognostic enrichment in clinical trials of sepsis interventions. Ultimately, prospective clinical trials will be needed to confirm and extend the findings presented here.

REFERENCES

1. Singer, M. et al. The Third International Consensus Definitions for Sepsis and Septic Shock (Sepsis-3). *JAMA* 315, 801 (2016).
2. Torio, C. M. (ahrq) & Andrews, R. M. (ahrq). National Inpatient Hospital Costs: The Most Expensive Conditions by Payer, 2011. HCUP Statistical Brief #160. (2013).
3. Liu, V. et al. Hospital Deaths in Patients With Sepsis From 2 Independent Cohorts. *JAMA* (2014). doi:10.1001/jama.2014.5804
4. Kaukonen, K. M., Bailey, M., Pilcher, D., Cooper, D. J. & Bellomo, R. Systemic inflammatory response syndrome criteria in defining severe sepsis. *N. Engl. J. Med.* 372, 1629-1638 (2015).
5. Opal, S. M., Dellinger, R. P., Vincent, J. L., Masur, H. & Angus, D. C. The next generation of sepsis clinical trial designs: what is next after the demise of recombinant human activated protein C?*. *Crit. Care Med.* 42, 1714-1721 (2014).
6. Cohen, J. et al. Sepsis: a roadmap for future research. *Lancet Infect. Dis.* 15, 581-614 (2015).
7. Shankar-Hari, M. et al. Developing a New Definition and Assessing New Clinical Criteria for Septic Shock: For the Third International Consensus Definitions for Sepsis and Septic Shock (Sepsis-3). *JAMA* 315, 775-787 (2016).
8. Abraham, E. New Definitions for Sepsis and Septic Shock: Continuing Evolution but With Much Still to Be Done. *JAMA* 315, 757-759 (2016).
9. Bermejo-Martin, J. F., Tamayo, E., Andaluz-Ojeda, D., Fernández, M. M.- & Almansa, R. Characterising Systemic Immune Dysfunction Syndrome (SIDS) to fill in the gaps of SEPSIS-2 and SEPSIS-3 definitions. *Chest (Accepted)*
10. Sweeney, T. E. & Wong, H. R. Risk Stratification and Prognosis in Sepsis: What Have We Learned from Microarrays? *Clin. Chest Med.* 37, 209-218 (2016).
11. Almansa, R. et al. Transcriptomic correlates of organ failure extent in sepsis. *J. Infect.* 70, 445-456 (2015).
12. Wong, H. R. et al. Developing a clinically feasible personalized medicine approach to pediatric septic shock. *Am. J. Respir. Crit. Care Med.* 191, 309-315 (2015).
13. Davenport, E. E. et al. Genomic landscape of the individual host response and outcomes in sepsis: a prospective cohort study. *Lancet Respir Med* (2016). doi:10.1016/S2213-2600(16)00046-1
14. Parnell, G. et al. Aberrant cell cycle and apoptotic changes characterise severe influenza A infection—a meta-analysis of genomic signatures in circulating leukocytes. *PLoS One* 6, e17186 (2011).
15. Parnell, G. P. et al. Identifying key regulatory genes in the whole blood of septic patients to monitor underlying immune dysfunctions. *Shock* 40, 166-174 (2013).
16. Wong, H. R. et al. Genome-level expression profiles in pediatric septic shock indicate a role for altered zinc homeostasis in poor outcome. *Physiol. Genomics* 30, 146-155 (2007).
17. Tsalik, E. L. et al. An integrated transcriptome and expressed variant analysis of sepsis survival and death. *Genome Med.* 6, 111 (2014).
18. Bolignano, D. et al. Prognostic models in the clinical arena. *Aging Clin. Exp. Res.* 24, 300-304 (2012).

19. Guinney, J. et al. Prediction of overall survival for patients with metastatic castration-resistant prostate cancer: development of a prognostic model through a crowdsourced challenge with open clinical trial data. *Lancet Oncol.* (2016). doi:10.1016/S1470-2045(16)30560-5
20. Sieberts, S. K. et al. Crowdsourced assessment of common genetic contribution to predicting anti-TNF treatment response in rheumatoid arthritis. *Nat. Commun.* 7, 12460 (2016).
21. Allen, G. I. et al. Crowdsourced estimation of cognitive decline and resilience in Alzheimer's disease. *Alzheimers. Dement.* 12, 645-653 (2016).
22. Noren, D. P. et al. A Crowdsourcing Approach to Developing and Assessing Prediction Algorithms for AML Prognosis. *PLoS Comput. Biol.* 12, e1004890 (2016).
23. Saez-Rodriguez, J. et al. Crowdsourcing biomedical research: leveraging communities as innovation engines. *Nat. Rev. Genet.* 17, 470-486 (2016).
24. Barrett, T. et al. NCBI GEO: archive for functional genomics data sets—update. *Nucleic Acids Res.* 41, D991-5 (2013).
25. Parkinson, H. et al. ArrayExpress—a public database of microarray experiments and gene expression profiles. *Nucleic Acids Res.* 35, D747-50 (2007).
26. Spence, R. P. et al. Validation of Virulence and Epidemiology DNA Microarray for Identification and Characterization of *Staphylococcus aureus* Isolates. *J. Clin. Microbiol.* 46, 1620-1627 (2008).
27. Howrylak, J. A. et al. Discovery of the gene signature for acute lung injury in patients with sepsis. *Physiol. Genomics* 37, 133-139 (2009).
28. Pankla, R. et al. Genomic transcriptional profiling identifies a candidate blood biomarker signature for the diagnosis of septicemic melioidosis. *Genome Biol.* 10, R127 (2009).
29. Berdal, J. E. et al. Excessive innate immune response and mutant D222G/N in severe A (H1N1) pandemic influenza. *J. Infect.* 63, 308-316 (2011).
30. Dolinay, T. et al. Inflammasome-regulated cytokines are critical mediators of acute lung injury. *Am. J. Respir. Crit. Care Med.* 185, 1225-1234 (2012).
31. Lill, M. et al. Peripheral blood RNA gene expression profiling in patients with bacterial meningitis. *Front. Neurosci.* 7, 33 (2013).
32. Kangelaris, K. N. et al. Increased expression of neutrophil-related genes in patients with early sepsis-induced ARDS. *Am. J. Physiol. Lung Cell. Mol. Physiol.* 308, L1102-13 (2015).
33. Bermejo-Martin, J. F. et al. Host adaptive immunity deficiency in severe pandemic influenza. *Crit. Care* 14, R167 (2010).
34. Ahn, S. H. et al. Gene expression-based classifiers identify *Staphylococcus aureus* infection in mice and humans. *PLoS One* 8, e48979 (2013).
35. Tsalik, E. L. et al. Host gene expression classifiers diagnose acute respiratory illness etiology. *Sci. Transl. Med.* 8, 322ra11 (2016).
36. Irwin, A. D. et al. Novel biomarker combination improves the diagnosis of serious bacterial infections in Malawian children. *BMC Med. Genomics* 5, 13 (2012).
37. Kwan, A., Hubank, M., Rashid, A., Klein, N. & Peters, M. J. Transcriptional instability during evolving sepsis may limit biomarker based risk stratification. *PLoS One* 8, e60501 (2013).
38. Raman, S. et al. Oxidative phosphorylation gene expression falls at onset and throughout the development of meningococcal sepsis-induced multi-organ failure in children. *Intensive Care Med.* 41, 1489-1490 (2015).
39. Sweeney, T. E., Shidham, A., Wong, H. R. & Khatri, P. A comprehensive time-course-based multicohort analysis of sepsis and sterile inflammation reveals a robust diagnostic gene set. *Sci. Transl. Med.* 7, 287ra71 (2015).
40. Almansa, R. et al. Transcriptomic evidence of impaired immunoglobulin G production in fatal septic shock. *J. Crit. Care* 29, 307-309 (2014).
41. Johnson, W. E., Li, C. & Rabinovic, A. Adjusting batch effects in microarray expression data using empirical Bayes methods. *Biostatistics* 8, 118-127 (2006).
42. Seok, J. et al. Genomic responses in mouse models poorly mimic human inflammatory diseases. *Proc. Natl. Acad Sci. U.S.A.* 110, 3507-3512 (2013).
43. Gautier, L., Cope, L., Bolstad, B. M. & Irizarry, R. A. affy—analysis of Affymetrix GeneChip data at the probe level. *Bioinformatics* 20, 307-315 (2004).
44. Ritchie, M. E. et al. limina powers differential expression analyses for RNA-sequencing and microarray studies. *Nucleic Acids Res.* 43, e47-e47 (2015).
45. Law, C. W., Yunshun, C., Wei, S. & Smyth, G. K. voom: precision weights unlock linear model analysis tools for RNA-seq read counts. *Genome Biol.* 15, R29 (2014).
46. Sweeney, T. E., Braviak, L., Tato, C. M. & Khatri, P. Genome-wide expression for diagnosis of pulmonary tuberculosis: a multicohort analysis. *Lancet Respir Med* 4, 213-224 (2016).
47. Kester, A. D. & Buntinx, F. Meta-analysis of ROC curves. *Med. Decis. Making* 20, 430-439 (2000).
48. The Gene Ontology Consortium. Gene Ontology Consortium: going forward. *Nucleic Acids Res.* 43, D1049-D1056 (2014).
49. Fabregat, A. et al. The Reactome pathway Knowledgebase. *Nucleic Acids Res.* 44, D481-7 (2016).
50. Milacic, M. et al. Annotating cancer variants and anticancer therapeutics in reactome. *Cancers* 4, 1180-1211 (2012).
51. Friedman, J., Hastie, T. & Tibshirani, R. Regularization Paths for Generalized Linear Models via Coordinate Descent. *J. Stat. Softw.* 33, 1-22 (2010).
52. Wright, M. N. & Ziegler, A. ranger: A Fast Implementation of Random Forests for High Dimensional Data in C++ and R. arXiv [stat.ML] (2015).
53. Mathias, B. et al. Human Myeloid-derived Suppressor Cells are Associated With Chronic Immune Suppression After Severe Sepsis/Septic Shock. *Ann. Surg.* (2016). doi:10.1097/SLA.0000000000001783
54. Pham, C. T. N. Neutrophil serine proteases: specific regulators of inflammation. *Nat. Rev. Immunol.* 6, 541-550 (2006).
55. Manfredi, A. A., Covino, C., Rovere-Querini, P. & Maugeri, N. Instructive influences of phagocytic clearance of dying cells on neutrophil extracellular trap generation. *Clin. Exp. Immunol.* 179, 24-29 (2015).
56. Masuda, S. et al. NETosis markers: Quest for specific, objective, and quantitative markers. *Clin. Chim. Acta* 459, 89-93 (2016).
57. Nalos, M. et al. Transcriptional reprogramming of metabolic pathways in critically ill patients. *Intensive Care Med Exp* 4, 21 (2016).
58. Tannahill, G. M. et al. Succinate is an inflammatory signal that induces IL-1β through HIF-1α. *Nature* 496, 238-242 (2013).
59. Yang, L. et al. PKM2 regulates the Warburg effect and promotes HMGB1 release in sepsis. *Nat. Commun.* 5, 4436 (2014).

60. Cheng, S.-C. et al. mTOR- and HIF-1α-mediated aerobic glycolysis as metabolic basis for trained immunity. *Science* 345, 1250684 (2014).
61. Liu, T. F. et al. Fueling the flame: bioenergy couples metabolism and inflammation. *J. Leukoc. Biol.* 92, 499-507 (2012).
62. Bierer, B. E., Li, R., Barnes, M. & Sim, I. A Global, Neutral Platform for Sharing Trial Data. *N. Engl. J. Med.* 374, 2411-2413 (2016).

TABLE 3

Up regulated genes

| pid | p-value |
|---|---|
| ARHGAP25 | 0.003889 |
| ASCL2 | 0.003284 |
| BIN1 | 0.006239 |
| CBFA2T3 | 0.007468 |
| CCL5 | 0.001922 |
| CD300A | 0.003762 |
| CD5 | 0.005673 |
| CDK10 | 0.006615 |
| CLEC10A | 0.009538 |
| CSK | 0.006925 |
| CST3 | 0.00915 |
| CTDSP2 | 0.009028 |
| CX3CR1 | 0.009912 |
| DGCR2 | 0.009412 |
| DHRS7B | 0.007579 |
| DOK2 | 0.001441 |
| FRAT2 | 0.003946 |
| HIST1H3H | 0.00714 |
| HLA-DPA1 | 0.005388 |
| HSPA6 | 0.009978 |
| IL6R | 0.006009 |
| ITGB1 | 0.006654 |
| ITPA | 0.005672 |
| KCNJ2 | 0.00608 |
| KLHL21 | 0.007547 |
| LDLRAP1 | 0.00967 |
| LY86 | 0.008037 |
| MNDA | 0.005697 |
| MTMR11 | 0.006504 |
| MXD4 | 0.002529 |
| PGRMC1 | 0.007762 |
| PKIA | 0.00643 |
| PLEKHA1 | 0.008547 |
| POLR2C | 0.00819 |
| POLRMT | 0.005873 |
| PPM1F | 0.005938 |
| RCBTB2 | 0.005966 |
| RIN1 | 0.009197 |
| RNF31 | 0.002479 |
| TARBP2 | 0.009932 |
| TBC1D22A | 0.009909 |
| TGFBI | 0.004088 |
| TST | 0.00621 |
| ZDHHC7 | 0.003281 |
| APOL2 | 0.002689 |
| CD1D | 0.009358 |
| CD3G | 0.004534 |
| EMR3 | 0.008587 |
| FCER1A | 0.00847 |
| RASSF4 | 0.008036 |

TABLE 4

Down regulated genes

| pid | p-value |
|---|---|
| ARID5B | 0.006721 |
| BPI | 0.007092 |
| CCNB1 | 0.003643 |
| CD24 | 0.002735 |

TABLE 4-continued

Down regulated genes

| pid | p-value |
|---|---|
| CEACAM8 | 0.009369 |
| CENPF | 0.002102 |
| CEP55 | 0.008494 |
| CKS2 | 0.001751 |
| CTSG | 0.008645 |
| DDIT4 | 0.00215 |
| GYPA | 0.002269 |
| HIPK2 | 0.009214 |
| KIAA0101 | 0.009413 |
| KIF14 | 0.003116 |
| MLF1IP | 0.00996 |
| MPO | 0.009564 |
| NEK2 | 0.006492 |
| NUSAP1 | 0.003742 |
| PDE4D | 0.005592 |
| PLK1 | 0.006068 |
| POLD3 | 0.009653 |
| PRC1 | 0.002117 |
| PSAT1 | 0.006409 |
| RAB11FIP2 | 0.007103 |
| RHAG | 0.005631 |
| SHCBP1 | 0.00222 |
| SPTA1 | 0.002355 |
| TOP2A | 0.007227 |
| TRIB1 | 0.003445 |
| YES1 | 0.009179 |
| BIRC5 | 0.008037 |
| CASC5 | 0.006839 |
| MKI67 | 0.009849 |
| TUBG1 | 0.001243 |

Example 2. Supplemental Materials: Mortality Prediction in Sepsis Via Gene Expression Analysis: A Community Approach HAI Dataset Descriptions Glue Grant (Burns & Trauma) Study: The Inflammation and Host Response to Injury Program (Glue Grant) whole blood/buffy coat cohorts[1] were treated as previously described[2]. The Glue Grant datasets contain two cohorts: patients admitted with severe trauma, and patients admitted with severe burns. The trauma cohorts further include two sub-cohorts, one which sampled buffy coat, and the other which sampled sorted cells; the sorted-cells cohort were excluded from further study. Trauma patients were sampled at the following days after admission: 0.5, 1, 4, 7, 14, 21, 28 days; Burn patients were sampled at admission, and then at the time of their burn operations. The Glue Grant patients were classified as 'infected' if they had a nosocomial infection (pneumonia, urinary tract infection, catheter-related bloodstream infection, etc.), a surgical infection (excluding superficial wound infections), or underwent surgery for perforated viscus. In burn patients, burn wound cultures of <100 CFU/g were not considered as infections. Only patients with samples drawn within ±24 hours of the day of diagnosis of infection were included. The initial 24 hours after admission was not included, as the index admissions were not for infectious causes. All deaths within 30 days were scored as deaths, regardless of cause. Use of the Glue Grant was approved by both the Glue Grant Consortium and the Stanford University IRB (protocol 29798).

Duke Hospital-Acquired Infection (HAI) Study: This prospective, multi-center, observational cohort study enrolled patients >18 years of age hospitalized within the medical or surgical wards, intensive care units, or step-down units of participating medical centers at Duke University Health System, Duke Regional Hospital, Durham Veterans Affairs Medical Center, and the University of North Carolina-Chapel Hill Hospital System. The purpose of the study was to understand the clinic-molecular risk factors and manifestations of HAI, inclusive of ventilator-associated pneumonia (VAP) and non-VAP HAI. Serial samples were obtained including pre- and post-sepsis onset. For the purposes of this analysis, we focused only on the time point corresponding to sepsis onset, as determined by a clinical adjudication process.

Prognostic Model Analysis Descriptions

Figure 3:
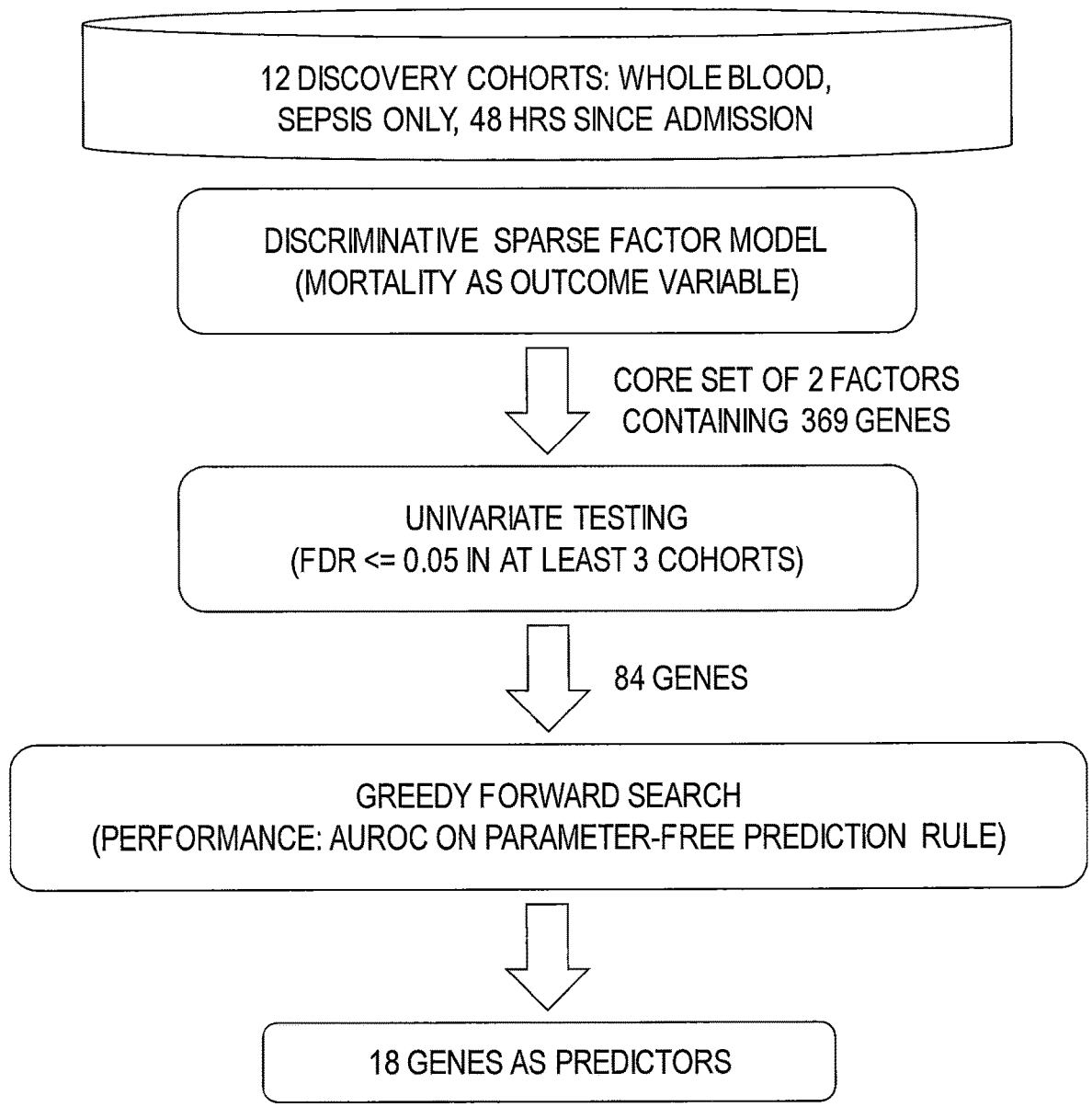
FIG. 3 is a schematic of workflow of discovery of the Duke model.
Figure 4:
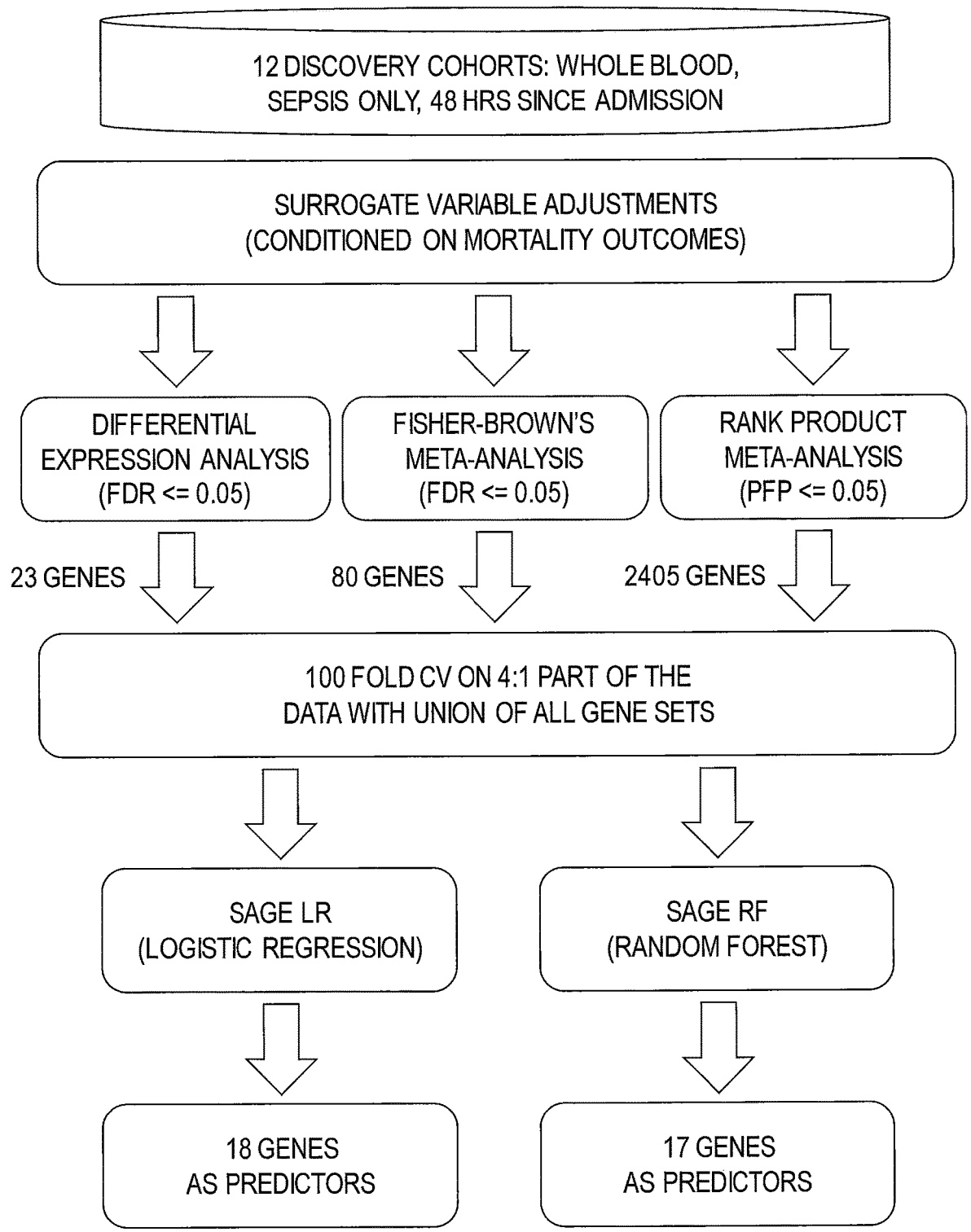
FIG. 4 is a schematic workflow of discovery of the Sage LR and Sage RF models.

Duke University: We propose a two-step process for identifying signatures of mortality in patients with sepsis. As seen in FIG. 3, the first step consists of a discriminative factor model[3] that attempts to jointly estimate the covariance structure of the data from a low-rank representation consisting of sparse factors, while also producing a sparse predictive model of mortality based on the latent factor scores also estimated by the model. The model has a clear interpretation by virtue of its sparseness property, each factor defines a subset of genes and the predictive model identifies which factors are discriminative (associated) with mortality. In addition, since the model captures the covariance structure of the data, factors not associated with mortality can often be found to be associated with other large sources of variation such as batch effects and/or demographic features. One known disadvantage of sparse factor models is that although it produces sparse factors, the size of the factors is usually in the hundreds of genes, which is less than ideal in applications were translation to targeted platforms admittedly require small gene signatures.

The second step of our methodology consists of down-selecting from the subset(s) of genes deemed by the factor model as discriminative of mortality, we call this collection of genes our core set. To this end, we perform univariate testing (1-way ANOVA) on each of the genes in the core set, individually for each discovery set to better quantify within-cohort mortality associations. Next, we filter-out genes not statistically significant in a proportion of the discovery sets (25% or 3 studies in the experiments) to then optimize the gene signature by greedy forward search on the remaining genes while sorting them by maximum raw p-value across discovery cohorts. The best signature is one such that the weighted average AUC is maximum. The prediction rule of our final predictive model is parameter-free and it is defined as the geometric mean of the up-regulated genes minus the geometric mean of the down-regulated genes in the original scale of the data, i.e., prior log-transformation. Note that this prediction rule is used during the greedy search but is not part of the sparse predictive model of our factor model. We opted for a parameter-free prediction rule as opposed to a parametric model, e.g., logistic regression, to simplify the final model and to make it less dependent on the scale of the data.

We applied this method to identify gene signatures associated with mortality in patients with sepsis. The model estimated 16 factors from which only two were statistically significant with respect to survival status at FDR<0.05. This discriminative factor consisted of 369 genes that form our signature core set. In order to obtain a smaller signature and a parameter-free classification model, we performed univariate testing on each one of the 12 discovery sets while restricting genes to our core set. We discarded genes that were not statistically significant at the p<0.05 level in at least 3 discovery sets (84 of 369). Next we optimized the gene signature by greedy search on the remaining 84 genes sorted by raw p-value across cohorts and using AUC as the performance metric. The greedy algorithm resulted in a final 18 gene set down-selected from the original 84 core set, from which 6 were up-regulated in non-survivors (CEACAM8, TRIB1, CKS2, MKI67, POLD3 and PLK1), while 12 were down-regulated in non-survivors (TGFBI, LY86, CST3, CBFA2T3, RCBTB2, TST, CX3CR1, CD5, MTMR11, CLEC10A, EMR3 and DHRS7B).

Sage LR and RF: Data Adjustments: For the purpose of selecting features that are relevant to mortality alone, we adjusted each cohort using a surrogate variable analysis (SVA)[4] conditioned on mortality status. This step avoids feature sets that could be confounded with other known and unknown covariates such as gender, age, severity and batch effects. Therefore, for each cohort, for each gene, we fit a regression model with mortality (known covariate) and surrogate variables (unknown covariates). The resulting residuals of the model is added back to the mortality coefficients and used for all downstream predictions.

Feature Reduction: Machine learning algorithms tend to perform better with reduced feature space[5]. Therefore, SVA adjusted data sets with 9340 genes expressed in all the 12 different discovery/training cohorts is reduced to a smaller feature set using three different methodologies. (i) First method fits a regression model for every gene in each cohort with mortality (as a dependent variable) and the resulting coefficients were tested for differential expression between survivors and nonsurvivors. This method results in 23 differentially expressed genes in all the 12 discovery cohorts at an FDR of 0.05. This approach, considering a maximum p-value of a gene in all studies, is a stringent criterion for selection. (ii) The second approach combines differential expression p-values for each gene in every cohort using Fisher's chi-squared statistics with a Brown's correction for non-independence/correlated effects between different cohorts. This approach is moderately conservative and results in 80 genes for prediction at an FDR of 0.05. (iii) The third approach is a rank produce methodology were each gene in a given sample were relatively ranked according to their expression values and the ranks across samples were combined using a rank product. The significance of the detection is assessed by a non-parametric permutation test. At an FDR of 0.05 this method results in 2405 genes across 12 different discovery cohorts. Finally, we took intersection of three methods resulting in 2367 unique genes from the 9340 as significant features for our multi-cohort analysis.

Model training: SVA adjusted gene expression of 2367 genes in 12 different cohorts were used to train a penalized logistic regression (sage LR)[8] and random forest (Sage RF)[9] models to predict nonsurvivors of sepsis from survivors. Discovery set were split into 100 different partitions of 80%-20% of training data and only the 80% of training data was used to train the models. Coefficients or variable importance scores for every gene in each model is relatively ranked and combined across all 100 splits to obtain a final ranking. 897 and 327 genes were considered as predictors in at least one of the 100 different Sage LR or Sage RF models, respectively.

Model pruning: All selected features from the 100 models may or may not be relevant. Therefore, as a final feature selection process, we pruned the above models based on the relative ranking of coefficients obtained from 100 different models and using a BIC criteria[10], which penalizes for increased model complexity. In the end, we obtain 9 up and 9 down regulated genes in Sage LR and 13 up and 4 down regulated genes in Sage RF models as predictors of mortality.

Sage LR: SVA adjusted data sets were used to infer gene signatures associated with mortality. As explained in Supplementary Methods 9340 genes that were commonly expressed in all the 12 different discovery cohorts were reduced to a smaller feature set using three different methodologies. At an FDR of 0.05, (i) 23 genes were differentially expressed in all the 12 discovery cohorts, (ii) combining differential expression analysis of 12 discovery cohorts resulted in 80 genes at an FDR of 0.05, (iii) rank product based differential expression in all 12 cohorts resulted in 2405 significant genes. Overall, we took 2367 significantly differentially expressed genes which were at least selected by one method as features for our multi-cohort analysis. Later, a penalized logistic regression algorithm was used to choose reduced genomic features from the selected 2367 genes. This resulted in a 18 gene model for predicting mortality in non-survivors at a summary AUROC of 0.79, 0.76 and 0.81 in the discovery, validation and HAI cohorts, respectively. These 18 genes include 9 up-regulated (CFD, DDIT4, DEFA4, IFI27, IL1R2, IL8, MAFF, OCLN, RGS1) and 9 down-regulated (AIM2, APH1A, CCR2, EIF5A, GSTM1, HIST1H3H, NT5E, RAB40B, VNN3) in nonsurvivors.

Sage RF: Like the Sage LR model, the Sage RF model used 2367 significantly differentially expressed genes which were at least selected by one of the method as features for our multi-cohort analysis. In contrast to penalized logistic regression, Sage RF model used penalized random forest algorithm to reduce the set of features that predicts mortality. In general, sage RF model displayed near perfect prediction in all the discovery data, with a summary AUROC of 1. However, the performance decreased in the validation data sets and shown significantly reduced performance in the HAI sets. This model resulted in an imbalanced 17 gene set with 13 (B4GALT4, BPI, CD24, CEP55, CTSG, DDIT4, G0S2, MPO, MT1G, NDUFV2, PAM, PSMA6, SEPP1) of them up-regulated in non-survivors and 4 (ABCB4, CTSS, IKZF2, NT5E) down-regulated in non-survivors.

Stanford University: After selecting the input datasets, we combined effect sizes within cohorts using Hedges' $g^{11}$, and then evaluated summary effects with a DerSimonian-Laird meta-analysis[12]. Significance thresholds were set at a false discovery rate (FDR) of 0.05, with a summary effect size greater than 1.3 fold (in non-log space).

We next performed a meta-regression analysis in the cohorts which supplied phenotype data of clinical severity and age. For each cohort, for each gene, the model was a regression on mortality (dependent) as a function of clinical severity plus age plus gene expression level. To keep the scales between datasets similar, (1) all clinical severity scores were converted to log-odds mortality, based on models in their describing papers, and (2) all datasets were ComBat-normalized[4] together prior to meta-analysis (this method resets the location and scale of each gene, but within-cohort differences are preserved). The meta-regression was carried out using the closed-form method-of-moments random-effects model variation[13] of the synthesis-of-slopes regression method described by Becker and Wu (2007)[14]. Thus, in this case, a gene was considered to be significant if it had statistically conserved regression coefficients (betas) across all cohorts for the prediction of mortality independent of clinical severity and age. An uncorrected p value<0.01 was deemed significant.

In the final step of the analysis, we took as significant the union of the gene sets deemed to be significant both by standard multi-cohort analysis and by meta-regression. These genes were then used in a greedy iterated search model, where a greedy forward search was allowed to run to completion, followed by a greedy backward search, and then another greedy forward search. This method iterated until it reached a stable gene set. Only the discovery datasets were used in the search, and the functions maximized the weighted AUC, which is the sum of the AUC of each discovery dataset multiplied by its sample size.

In the greedy search, and with the final gene set, the gene score is defined as the geometric mean of the gene expression level for all positive genes minus the geometric mean of the gene expression level of all negative genes multiplied by the ratio of counts of positive to negative genes. This was calculated for each sample in a dataset separately. Genes not present in an entire dataset were excluded; genes missing for individual samples were set to one.

Figure 5:
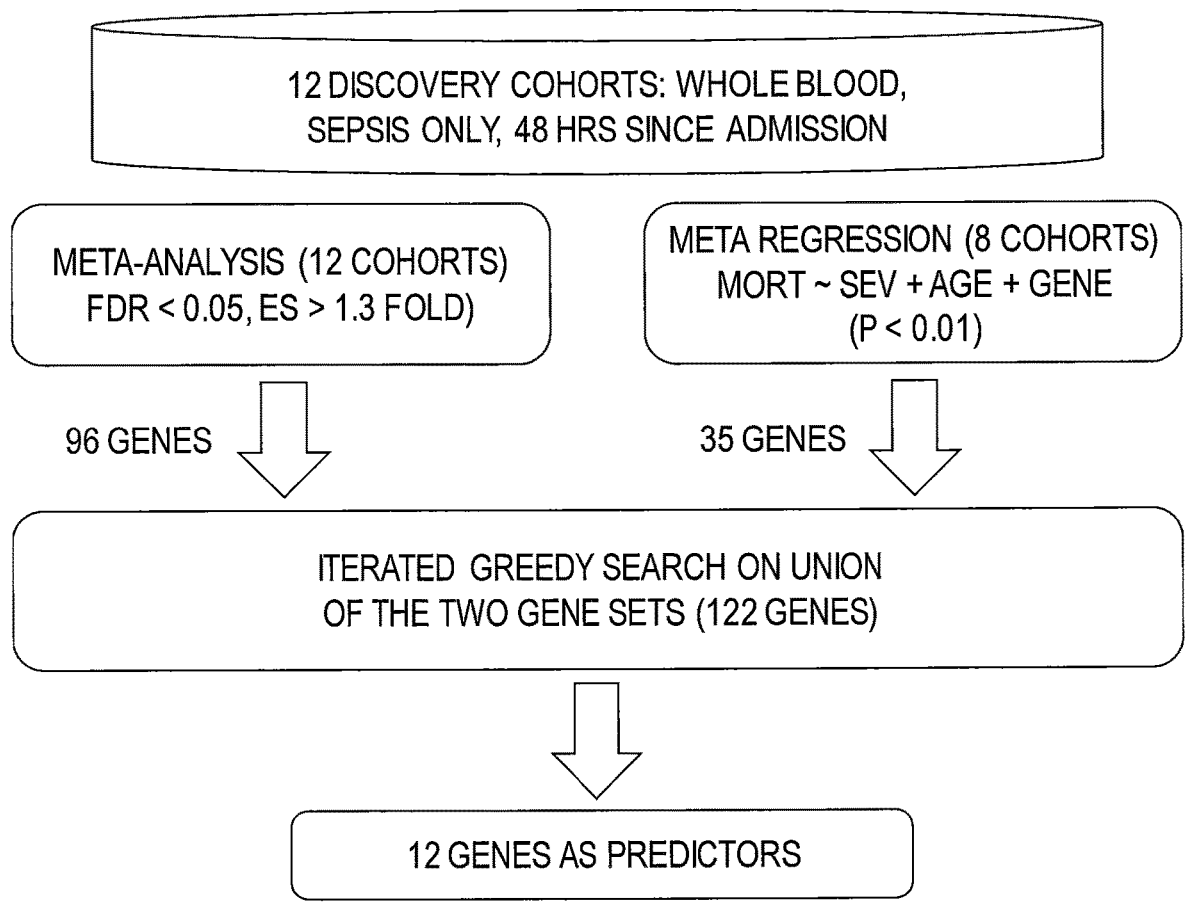
FIG. 5 is a schematic of workflow of discovery of the Stanford model.

We applied two analytic methods to discover genes significantly associated with mortality (FIG. 5). In the first, we performed multi-cohort meta-analysis for differential gene expression between survivors and nonsurvivors at admission, yielding 96 genes significant at FDR<0.05 and effect size >1.3-fold. In the second analysis, we performed synthesis-of-slopes random-effects meta-regression for mortality as a logistic function of clinical severity, age, and gene expression. This yielded 35 genes significant at p<0.01. Notably, the top three most-significant genes in the meta-regression were all from the same pathway, namely, neutrophil azurophilic granules: DEFA4, CTSG, and MPO. The union of the meta-analysis and meta-regression gene sets was 122 genes, which we took as our 'significant' gene list.

We next used the 122-gene list to perform an iterated greedy search on the 12 discovery datasets, trying to find a gene list which maximized diagnostic performance, as measured by weighted AUC. Briefly, the algorithm iterates between a forward and backward greedy search, until it converges on a gene list. This algorithm is designed to find maxima closer to the global maximum than a simple forward search. The algorithm ran to completion, producing a 12-gene set. The genes upregulated in patients with mortality were: DEFA4, CD163, PER1, RGS1, HIF1A, SEPP1, C11orf74, and CIT, and the downregulated genes were: LY86, TST, OR52R1, and KCNJ2.

Ensemble Model: The aim of the ensemble model is to aggregate the classifications submitted by the individual four models, by effectively leveraging the consensus as well as diversity among these predictions. We performed a stacking-based penalized SVM, a heterogeneous ensemble methodology. This method learns a meta-classifier (second level predictor) with the prediction scores from the four base classifiers. In order to reduce the over-fitting of the ensemble classifier, the training set for classifications were generated through a leave-one-cohort-out cross-validation procedure applied to all the discovery cohorts. To address the potential calibration issue, we also investigated two different normalization procedures; z-score based (mean=0, SD=1) and rank based scaling (maximum=1, minimum=0), applied to the raw base classification scores. Normalized scores were then used to train a meta-classifier model. To this end, we used penalisedSVM[15] package in R with elastic SCAD penalty.

Supplemental Tables

SUPPLEMENTARY TABLE 1

Summary AUROCs for genomic models

| Cohort Category | Parameter | Duke | Sage LR | Sage RF | Stanford |
|---|---|---|---|---|---|
| Discovery | Summary | 0.73 | 0.79 | 1.0 | 0.85 |
| | 95% CI | 0.62-0.82 | 0.69-0.87 | 1.0-1.0 | 0.77-0.91 |
| | Range | 0.46-0.96 | 0.69-0.87 | 1.0-1.0 | 0.72-1.0 |

SUPPLEMENTARY TABLE 1-continued

Summary AUROCs for genomic models

| Cohort Category | Parameter | Duke | Sage LR | Sage RF | Stanford |
|---|---|---|---|---|---|
| Validation | Summary | 0.88 | 0.76 | 0.87 | 0.89 |
|  | 95% CI | 0.62-0.98 | 0.64-0.86 | 0.61-0.97 | 0.57-0.98 |
|  | Range | 0.70-1.0 | 0.70-0.95 | 0.64-1.0 | 0.79-0.99 |
| HAI | Summary | 0.87 | 0.81 | 0.53 | 0.87 |
|  | 95% CI | 0.62-0.98 | 0.64-0.86 | 0.61-0.97 | 0.57-0.98 |
|  | Range | 0.70-1.0 | 0.70-0.95 | 0.64-1.0 | 0.79-0.99 |

SUPPLEMENTARY TABLE 2

Individual AUROCs for genomic models

| Cohort ID | Duke | Sage LR | Sage RF | Stanford |
|---|---|---|---|---|
| *Discovery cohorts* | | | | |
| E-MEXP-3567 | 0.806 | 0.556 | 1.000 | 0.833 |
| E-MEXP-3850 | 0.947 | 0.916 | 1.000 | 1.000 |
| E-MTAB-1548 | 0.818 | 0.867 | 1.000 | 0.847 |
| GSE10474 | 0.463 | 0.698 | 1.000 | 0.719 |
| GSE13015a | 0.787 | 0.831 | 1.000 | 0.835 |
| GSE13015b | 0.964 | 0.804 | 1.000 | 0.804 |
| GSE27131 | 0.700 | 0.700 | 1.000 | 1.000 |
| GSE32707 | 0.514 | 0.712 | 0.996 | 0.810 |
| GSE40586 | 0.632 | 0.868 | 1.000 | 0.842 |
| GSE63042 | 0.689 | 0.879 | 1.000 | 0.784 |
| GSE66099 | 0.806 | 0.916 | 1.000 | 0.881 |
| GSE66890 | 0.802 | 0.711 | 1.000 | 0.834 |
| *Validation cohorts* | | | | |
| E-MTAB-4421 | 0.695 | 0.810 | 0.714 | 0.829 |
| GSE21802 | 0.714 | 0.750 | 0.643 | 0.786 |
| GSE33341 | 1.000 | 0.949 | 1.000 | 0.990 |
| GSE54514 | 0.936 | 0.701 | 0.902 | 0.816 |
| GSE63990 | 0.802 | 0.833 | 0.859 | 0.805 |

SUPPLEMENTARY TABLE 2-continued

Individual AUROCs for genomic models

| Cohort ID | Duke | Sage LR | Sage RF | Stanford |
|---|---|---|---|---|
| *HAI Cohorts* | | | | |
| Duke HAI | 0.905 | 0.963 | 0.522 | 0.875 |
| Glue Burns D1-D30 | 0.850 | 0.731 | 0.656 | 0.769 |
| Glue Trauma D1-D30 | 1.000 | 0.938 | 0.333 | 1.000 |
| UF P50 12H | 0.573 | 0.652 | 0.400 | 0.682 |

SUPPLEMENTARY TABLE 3

Ensemble model performance characteristics

| Cohort ID | AUROC (NS) | AUPR (NS) | PPV (NS) | NPV (NS) | PPV (S) | NPV (S) |
|---|---|---|---|---|---|---|
| *Discovery cohorts* | | | | | | |
| EMEXP3567 | 0.667 | 0.606 | 1.000 | 0.667 | 0.545 | 1.000 |
| EMEXP3850 | 0.937 | 0.685 | 1.000 | 0.950 | 0.783 | 0.000 |
| EMTAB1548 | 0.899 | 0.684 | 1.000 | 0.685 | 0.671 | 0.000 |
| GSE10474 | 0.711 | 0.577 | 1.000 | 0.733 | 0.690 | 0.500 |
| GSE13015a | 0.881 | 0.624 | 1.000 | 0.778 | 0.723 | 0.000 |
| GSE13015b | 0.804 | 0.623 | 0.778 | 1.000 | 1.000 | 0.500 |
| GSE27131 | 1.000 | 0.500 | 1.000 | 1.000 | 0.667 | 0.000 |
| GSE32707 | 0.788 | 0.578 | 0.455 | 1.000 | 1.000 | 0.357 |
| GSE40586 | 0.842 | 0.098 | 1.000 | 0.950 | 0.900 | 0.000 |
| GSE63042 | 0.892 | 0.731 | 1.000 | 0.776 | 0.728 | 0.000 |
| GSE66099 | 0.924 | 0.687 | 1.000 | 0.886 | 0.859 | 0.000 |
| GSE66890 | 0.862 | 0.542 | 1.000 | 0.782 | 0.750 | 0.000 |
| Average | 0.851 | 0.578 | 0.936 | 0.851 | 0.776 | 0.196 |
| Std.Dev | 0.095 | 0.165 | 0.165 | 0.127 | 0.139 | 0.325 |
| *Validation cohorts* | | | | | | |
| EMTAB4421 | 0.743 | 0.523 | 0.800 | 0.824 | 1.000 | 0.333 |
| GSE21802 | 0.786 | 0.519 | 0.571 | 1.000 | 1.000 | 0.400 |
| GSE33341 | 1.000 | 0.500 | 1.000 | 1.000 | 0.960 | 0.000 |
| G5E54514 | 0.791 | 0.420 | 0.474 | 1.000 | 1.000 | 0.281 |
| GSE63990 | 0.714 | 0.180 | 1.000 | 0.928 | 0.917 | 0.100 |
| Average | 0.807 | 0.428 | 0.769 | 0.950 | 0.975 | 0.223 |
| Std.Dev | 0.113 | 0.145 | 0.242 | 0.077 | 0.037 | 0.167 |

SUPPLEMENTARY TABLE 4

AUPR for genomic models (Individual cohorts)

| Cohort ID | Duke | Sage LR | Sage RF | Stanford |
|---|---|---|---|---|
| *Discovery cohorts* | | | | |
| E-MEXP-3567 | 0.686 | 0.530 | 0.833 | 0.746 |
| E-MEXP-3850 | 0.616 | 0.475 | 0.800 | 0.800 |
| E-MTAB-1548 | 0.558 | 0.637 | 0.958 | 0.620 |
| GSE10474 | 0.321 | 0.525 | 0.909 | 0.594 |
| GSE13015a | 0.568 | 0.502 | 0.923 | 0.535 |
| GSE13015b | 0.816 | 0.600 | 0.857 | 0.623 |
| GSE27131 | 0.163 | 0.208 | 0.500 | 0.500 |
| GSE32707 | 0.333 | 0.533 | 0.938 | 0.658 |
| GSE40586 | 0.176 | 0.225 | 0.500 | 0.238 |
| GSE63042 | 0.378 | 0.670 | 0.964 | 0.555 |
| GSE66099 | 0.374 | 0.662 | 0.964 | 0.468 |
| GSE66890 | 0.541 | 0.408 | 0.929 | 0.597 |
| *Validation cohorts* | | | | |
| E-MTAB-4421 | 0.350 | 0.540 | 0.407 | 0.519 |
| GSE21802 | 0.442 | 0.519 | 0.392 | 0.519 |
| GSE33341 | 0.500 | 0.208 | 0.500 | 0.292 |
| GSE54514 | 0.694 | 0.372 | 0.713 | 0.613 |
| GSE63990 | 0.246 | 0.204 | 0.240 | 0.182 |

SUPPLEMENTARY TABLE 4-continued

AUPR for genomic models (Individual cohorts)

| Cohort ID | Duke | Sage LR | Sage RF | Stanford |
|---|---|---|---|---|
| HAI Cohorts | | | | |
| Duke HAI | 0.514 | 0.804 | 0.145 | 0.545 |
| Glue Burns D1-D30 | 0.491 | 0.205 | 0.144 | 0.172 |
| Glue Trauma D1-D30 | 0.000 | 0.250 | 0.015 | 0.000 |
| UF P50 12H | 0.085 | 0.157 | 0.054 | 0.129 |

SUPPLEMENTARY TABLE 5

AUROC with genomic features and clinical severity. Some gene model AUCs may differ from Supplementary Table 2 since samples without severity scores were dropped from this analysis.

| | Score Type | Severity Alone | Duke gene model | Duke joint | Sage LR gene model | Sage LR joint | Sage RF gene model | Sage RF joint | Stanford gene model | Stanford joint |
|---|---|---|---|---|---|---|---|---|---|---|
| Discovery Datasets | | | | | | | | | | |
| EMEXP3850 | PELOD | 1 | 0.947 | 1 | 0.916 | 1 | 1 | 1 | 1 | 1 |
| EMTAB1548 | SOFA | 0.735 | 0.817 | 0.843 | 0.863 | 0.87 | 1 | 1 | 0.849 | 0.863 |
| G5E10474 | APACHE II | 0.551 | 0.53 | 0.626 | 0.682 | 0.758 | 1 | 1 | 0.722 | 0.697 |
| G5E27131 | SAPS II | 1 | 0.7 | 1 | 0.7 | 1 | 1 | 1 | 1 | 1 |
| G5E32707 | APACHE II | 0.546 | 0.514 | 0.537 | 0.712 | 0.702 | 0.996 | 0.996 | 0.81 | 0.805 |
| GSE63042 | APACHE II | 0.774 | 0.679 | 0.797 | 0.866 | 0.868 | 1 | 1 | 0.742 | 0.815 |
| G5E66099 | PRISM | 0.781 | 0.806 | 0.84 | 0.916 | 0.913 | 1 | 1 | 0.881 | 0.892 |
| G5E66890 | APACHE II | 0.723 | 0.802 | 0.847 | 0.711 | 0.759 | 1 | 1 | 0.834 | 0.849 |
| Validation Datasets | | | | | | | | | | |
| EMTAB4421 | APACHE | 0.705 | 0.695 | 0.771 | 0.81 | 0.762 | 0.714 | 0.752 | 0.829 | 0.838 |
| GSE21802 | SOFA | 0.812 | 0.333 | 0.833 | 0.708 | 0.792 | 0.583 | 0.833 | 0.75 | 0.833 |
| GSE54514 | APACHE | 0.776 | 0.936 | 0.944 | 0.701 | 0.739 | 0.902 | 0.927 | 0.816 | 0.825 |
| HAI Datasets | | | | | | | | | | |
| Glue Burns D1-D30 | Denver score | 0.482 | 0.808 | 0.842 | 0.721 | 0.731 | 0.606 | 0.604 | 0.74 | 0.756 |
| Glue Trauma D1-D30 | MODS score | 0.927 | 1 | 1 | 0.938 | 0.979 | 0.667 | 0.958 | 1 | 1 |
| UF P50 12H | SOFA | 0.941 | 0.573 | 0.945 | 0.652 | 0.945 | 0.6 | 0.952 | 0.682 | 0.945 |

SUPPLEMENTARY TABLE 6

Agreement between models. Classification labels were obtained from study-wise thresholds corresponding to 90% sensitivity (non-survivors). Consensus corresponds to patients correctly classified by at least 3 of 4 models, whereas no consensus represents correct classifications by 1 or 2 models.

| Cohort ID | Always misclassified | No Consensus | Consensus |
|---|---|---|---|
| Discovery Cohorts | | | |
| GSE40586 | 0.0952 | 0.5238 | 0.3810 |
| GSE10474 | 0.5152 | 0.1818 | 0.3030 |
| GSE13015a | 0.0417 | 0.3542 | 0.6042 |
| GSE13015b | 0.0000 | 0.2000 | 0.8000 |
| GSE27131 | 0.0000 | 0.4286 | 0.5714 |
| GSE32707 | 0.0625 | 0.4792 | 0.4583 |
| GSE63042 | 0.1923 | 0.4615 | 0.3462 |
| GSE66099 | 0.0854 | 0.2915 | 0.6231 |
| GSE66890 | 0.2456 | 0.2456 | 0.5088 |
| EMTAB1548 | 0.1216 | 0.1622 | 0.7162 |
| EMEXP3567 | 0.0000 | 0.2500 | 0.7500 |
| EMEXP3850 | 0.0000 | 0.1250 | 0.8750 |
| Discovery Average | 11.33 +/- 14.94 | 30.86 +/- 13.86 | 57.81 +/- 18.49 |
| Validation Cohorts | | | |
| GSE54514 | 0.0857 | 0.2571 | 0.6571 |
| EMTAB4421 | 0.0909 | 0.2727 | 0.6364 |
| GSE21802 | 0.1818 | 0.0909 | 0.7273 |
| GSE33341 | 0.0000 | 0.0000 | 1.0000 |
| GSE63990 | 0.0429 | 0.2286 | 0.7286 |
| Validation Average | 8.03 +/- 6.76 | 16.99 +/- 11.91 | 74.99 +/- 15.58 |
| HAI Cohorts | | | |
| UF P50 12H | 0.2394 | 0.4930 | 0.2676 |
| Glue Trauma D1-D30 | 0.0000 | 0.0000 | 1.0000 |
| Glue Burns D1-D30 | 0.1087 | 0.3696 | 0.5217 |
| Duke HAI | 0.0000 | 0.3000 | 0.7000 |
| HAI Average | 8.70 +/- 11.38 | 29.06 +/- 20.95 | 62.23 +/- 30.80 |
| Total Average | 10.04 +/- 12.39 | 27.22 +/- 15.23 | 62.74 +/- 20.62 |

SUPPLEMENTARY TABLE 7

Genomic features of sepsis mortality (intersection from all models)

| Direction | Predictors |
|---|---|
| Up-regulated in mortality (31 genes) | DEFA4, CD163, PER1, RGS1, HIF1A, SEPP1, C11orf74, CIT, CFD, DDIT4, IFI27, IL1R2, IL8, MAFF, OCLN, B4GALT4, BPI, CD24, CEP55, CTSG, G0S2, MPO, MT1G, NDUFV2, PAM, PSMA6, TRIB1, CKS2, MKI67, POLD3, PLK1 |
| Down-regulated in mortality (27 genes) | LY86, TST, OR52R1, KCNJ2, AIM2, APH1A, CCR2, EIF5A, GSTM1, HIST1H3H, NT5E, RAB40B, VNN3, ABCB4, CTSS, IKZF2, TGFBI, CST3, CBFA2T3, RCBTB2, CX3CR1, CD5, MTMR11, CLEC10A, EMR3, DHRS7B, CEACAM8 |

SUPPLEMENTARY TABLE 8

Nominally enriched pathways. Significance was set at a p value ≤ 0.05 and gene sets were only included with at least 3 genes overlapping.

| Gene Set Name | p value (unadjusted) | Odds ratio |
|---|---|---|
| *Up regulated in non-survivors* | | |
| nuclear division (GO:0000280) | 2.25E−04 | 10.56 |
| organelle fission (GO:0048285) | 3.40E−04 | 9.62 |
| defense response to other organism (GO:0098542) | 3.70E−04 | 9.44 |
| negative regulation of growth (GO:0045926) | 2.00E−03 | 8.45 |
| response to molecule of bacterial origin (GO:0002237) | 3.15E−03 | 7.41 |
| response to hypoxia (GO:0001666) | 3.43E−03 | 7.24 |
| negative regulation of phosphorylation (GO:0042326) | 6.61E−03 | 5.97 |
| apoptotic signaling pathway (GO:0097190) | 8.35E−03 | 5.57 |
| negative regulation of protein modification process (GO:0031400) | 1.51E−02 | 4.64 |
| regulation of protein serine/threonine kinase activity (GO:0071900) | 1.56E−02 | 4.6 |
| negative regulation of phosphate metabolic process (GO:0045936) | 1.87E−02 | 4.34 |
| negative regulation of phosphorus metabolic process (GO:0010563) | 1.87E−02 | 4.34 |
| regulation of cytokine production (GO:0001817) | 2.51E−02 | 3.95 |
| *Up regulated in survivors* | | |
| response to wounding (GO:0009611) | 5.44E−03 | 9.38 |
| positive regulation of response to external stimulus (GO:0032103) | 9.68E−03 | 7.56 |
| regulation of inflammatory response (GO:0050727) | 1.46E−02 | 6.45 |
| positive regulation of defense response (GO:0031349) | 1.99E−02 | 5.72 |
| cytokine-mediated signaling pathway (GO:0019221) | 3.34E−02 | 4.65 |
| extracellular matrix organization (GO:0030198) | 3.75E−02 | 4.43 |
| cellular amino acid metabolic process (GO:0006520) | 4.42E−02 | 4.14 |

REFERENCES

1. Xiao, W. et al. A genomic storm in critically injured humans. *J. Exp. Med.* 208, 2581-2590 (2011).
2. Sweeney, T. E., Shidham, A., Wong, H. R. & Khatri, P. A comprehensive time-course-based multicohort analysis of sepsis and sterile inflammation reveals a robust diagnostic gene set. *Sci. Transl. Med.* 7, 287ra71 (2015).
3. Henao, R., Yuan, X. & Carin, L. Bayesian Nonlinear Support Vector Machines and Discriminative Factor Modeling. in *NIPS* (2014).
4. Leek, J. T., Johnson, W. E., Parker, H. S., Jaffe, A. E. & Storey, J. D. The sva package for removing batch effects and other unwanted variation in high-throughput experiments. *Bioinformatics* 28, 882-883 (2012).
5. Fefferman, C., Charles, F., Sanjoy, M. & Hariharan, N. Testing the manifold hypothesis. *J. Amer. Math. Soc.* 29, 983-1049 (2016).
6. Brown, M. B. 400: A Method for Combining Non-Independent, One-Sided Tests of Significance. *Biometrics* 31, 987 (1975).
7. Hong, F. et al. RankProd: a bioconductor package for detecting differentially expressed genes in meta-analysis. *Bioinformatics* 22, 2825-2827 (2006).
8. Friedman, J., Hastie, T. & Tibshirani, R. Regularization Paths for Generalized Linear Models via Coordinate Descent. *J. Stat. Softw.* 33, 1-22 (2010).
9. Liaw, A. & Wiener, M. Classification and Regression by randomForest. *R News* 2, 18-22 (2002).
10. in *Springer Series in Statistics* 211-237 (2008).
11. Hedges, L. V. Distribution Theory for Glass's Estimator of Effect Size and Related Estimators. *J. Educ. Behav. Stat.* 6, 107 (1981).
12. DerSimonian, R. & Laird, N. Meta-analysis in clinical trials. *Control. Clin. Trials* 7, 177-188 (1986).
13. Chen, H., Manning, A. K. & Dupuis, J. A method of moments estimator for random effect multivariate meta-analysis. *Biometrics* 68, 1278-1284 (2012).
14. Becker, B. J. & Meng-Jia, W. The Synthesis of Regression Slopes in Meta-Analysis. *Stat. Sci.* 22, 414-429 (2007).
15. Zhang, H. H., Aim, J., Lin, X. & Park, C. Gene selection using support vector machines with non-convex penalty. *Bioinformatics* 22, 88-95 (2006).

Example 3. Identification of Ventilator Acquired/Associated Pneumonia Via Gene Expression Analysis Whole blood transcriptomic (genome wide expression) profiling may be an effective way to detect patients with sepsis, including healthcare-associated infections such as ventilator associated pneumonia (VAP).

A prospective observational cohort study identified patients in a participating care unit who were at high risk of developing VAP by virtue of recent intubation and an expected duration of ventilation of greater than 48 hours. Such patients are referred to as "at-risk". We screened for eligible patients in emergency departments, intensive care units, step-down units, and other appropriate locations within the Duke University Health System, Durham Veterans Affairs Medical Center, and UNC Health Care. The target enrollment was 150 patients (50 patients per year or approximately 1/week) over 3 years.

At-risk subjects were monitored for suspected hospital acquired infection (HAI) including VAP, using pre-specified criteria such as fever and other signs and symptoms (see Transition Criteria in the protocol). Clinical information and biological samples were collected at protocol-defined intervals through Day 6. If no VAP or other HAI occurred in an "at-risk" subject, sample collection ended at Day 6 and this patient served as an uninfected control. However, if an HAI occurred within this window, the patient was followed for an additional seven days as part of the "at-risk" group-event phase. Clinical status was assessed on protocol-specified days. Vital status and clinical outcomes will be determined at Day 30 (measured from the time of enrollment or HAI event, whichever is later).

In order to differentiate a VAP-specific signature from a more general infection signature, we identified patients in participating care units who developed a suspected HAI. These patients served as the HAI (non-VAP) control group.

Enrollment criteria for these infected controls were the same as the transition criteria used for "at-risk" subjects entering the event phase. Target enrollment was 75 patients. These subjects were followed for 7 days, as well, resulting in a 1:1 ratio of at-risk subjects to HAI controls. HAI events consisted largely of central line-associated blood stream infection, surgical site infections, HAP, and *Clostridium difficile*-associated diarrhea.

Since the specific type of HAI was apparent at enrollment, an adjudication committee used prospectively collected clinical data to categorize patients into specific HAI groups. To make these categorizations, the committee incorporated clinical, microbiological, and radiographic data. The committee consisted of physicians with training in infectious diseases/microbiology and pulmonary/critical care.

We sought to identify host gene classifiers associated with development of ventilator associated pneumonia among intubated patients as compared with uninfected, intubated patients.

After subjects were clinically and microbiologically categorized, we submitted peripheral blood samples from these patients for RNA sequencing and proteomic analysis according to our standard protocol.

For sequence processing we mapped to hg19 reference sequence transcripts using tophat2. We retained transcripts with greater than or equal to 20 effective counts in at least 50% of the samples and the upper quartile were normalized.

We performed principal component analysis, including PC regression with technical and biological factors, as an exploratory analysis and identified sex and RIN as contributors to expression variation. For bivariable testing we Voom normalized with the analysis sample subset and tested each transcript and each principal component. We developed a Bayesian linear fixed effect model (variance shrinkage) including sex and RIN covariates. We discarded genes that were not statistically significant to the 0.05 level in at least 3 discovery sets. There were 307 transcripts with non-zero coefficients in any validation fold and 32 with non-zero coefficients in >50% of cross validation folds. We conducted moderated t-tests using "R" limma fit and eBayes function. For multivariable assessment, we log transformed the data and standardized by sex and RIN. We filtered either the top 5% variable genes, the top 5% mean expressed genes, or the top 100 differentially expressed genes. Analysis was performed using elastic net regularized regression with leave one out cross validation. The top performing model (mean expression) achieved a training AUC of 0.834. The optimized algorithm resulted in a downselected final 24 gene set. Of these 14 were down regulated in VAP (SIGLEC10, TSC22D3, RCN3, LST1, HBA1, FGR, TYMP, ATG16L2, CEACAM4, TYMP (alternate transcript), PECAM1, HMHA1, APOBEC3A, P2RX1) and 10 (PCBP1, TMBIM6, LASP1, KLF2, OS9, APMAP, CD14, NAMPT, NQO2, CDK5RAP2) were upregulated. We then assessed the behavior of the classifier over time. We first retrained the classifier using all training data. AUC for VAP at 1-2 days pre-infection was 0.766 and 1-2 days post-infection was 0.899. Over time there was resolution of the signature.

Early diagnosis of sepsis, including ventilator associated pneumonia, is now imminently possible using molecular tools like the one presented here. The discovery made here will serve as an improvement over existing clinical risk stratification tools and may also provide an improved ability to enrich clinical trials with the patients most likely to benefit.

Differential Expression of Individual Genes that Differentiate VAP from Uninfected Hospitalized Patients

| Transcript | Gene Symbol | Log Fold Change | P value | Description |
|---|---|---|---|---|
| NM_052961 | SLC26A8 | 1.286 | $5.9 \times 10^{-9}$ | Solute carrier fanmily 26 (anion exchanger), member 8 |
| NM_013363 | PCOLCE2 | 1.718 | $7.9 \times 10^{-7}$ | Procollagen C-endopeptidase enhancer 2 |
| NM_004566 | PFKFB3 | 4.266 | $2.9 \times 10^{-6}$ | 6-Phosphofructo-2-Kinase/Fructose-2,6-Bisphosphatase 3 |
| NM_052864 | TIFA | 4.247 | $7.1 \times 10^{-6}$ | Putative NF-Kappa-B-activating protein 20 |

Genes Included in Classifier that Discriminates Patients with VAP from those without Infection

| Down regulated in VAP | | | Up regulated in VAP | | |
|---|---|---|---|---|---|
| Ensembl ID | Gene Symbol | logFC | Ensembl ID | Gene Symbol | logFC |
| ENSG00000142512 | SIGLEC10 | −0.667 | ENSG00000169564 | PCBP1 | 0.227 |
| ENSG00000157514 | TSC22D3 | −0.62 | ENSG00000139644 | TMBIM6 | 0.241 |
| ENSG00000142552 | RCN3 | −0.598 | ENSG00000002834 | LASP1 | 0.294 |
| ENSG00000204482 | LST1 | −0.488 | ENSG00000127528 | KLF2 | 0.294 |
| ENSG00000206172 | HBA1 | −0.415 | ENSG00000135506 | OS9 | 0.357 |
| ENSG00000000938 | FGR | −0.255 | ENSG00000101474 | APMAP | 0.453 |
| ENSG00000025708 | TYMP | −0.21 | ENSG00000170458 | CD14 | 0.67 |
| ENSG00000168010 | ATG16L2 | −0.196 | ENSG00000105835 | NAMPT | 0.733 |
| ENSG00000105352 | CEACAM4 | −0.185 | ENSG00000124588 | NQO2 | 0.745 |
| ENSG00000025708 | TYMP | −0.167 | ENSG00000136861 | CDK5RAP2 | 0.989 |
| ENSG00000261371 | PECAM1 | −0.132 | | | |
| ENSG00000180448 | HMHA1 | −0.126 | | | |
| ENSG00000128383 | APOBEC3A | −0.115 | | | |

Refseq IDs

| | |
|---|---|
| NM_000442 | PECAM1 |
| NM_000558 | HBA1 |
| NM_000904 | NQO2 |
| NM_001015881 | TSC22D3 |
| NM_001042729 | FGR |
| NM_001113755 | TYMP |
| NM_001171161 | SIGLEC10 |
| NM_001174105 | CD14 |
| NM_001261421 | OS9 |
| NM_001271608 | LASP1 |
| NM_001272039 | CDK5RAP2 |
| NM_001817 | CEACAM4 |
| NM_001953 | TYMP |

-continued

| | |
|---|---|
| NM_002558 | P2RX1 |
| NM_003217 | TMBIM6 |
| NM_005746 | NAMPT |
| NM_006196 | PCBP1 |
| NM_016270 | KLF2 |
| NM_020531 | APMAP |
| NM_020650 | RCN3 |
| NM_033388 | ATG16L2 |
| NM_145699 | APOBEC3A |
| NM_205839_7 | LST1 |
| NR_047652 | HMHA1 |

Any patents or publications mentioned in this specification are indicative of the levels of those skilled in the art to which the present disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein is presently, representative of preferred embodiments, are exemplary, and are not intended as limitations on the scope of the invention. Changes therein and other uses will occur to those skilled in the art which are encompassed within the spirit of the present disclosure as defined by the scope of the claims.

We claim:

1. A method for determining an increased risk of mortality in a subject with sepsis or suspected of having sepsis, comprising:
   providing a biological sample of the subject; and
   measuring on a platform differential expression of a pre-defined set of genes in the biological sample, wherein said differential expression comprises:
   i) an increase in expression of the genes: TRIB1, CKS2, MKI67, POLD3, and PLK1; and
   ii) a decrease in expression of the genes: TGFBI, LY86, CST3, CBFA2T3, RCBTB2, TST, CX3CR1, CD5, MTMR11, CLEC10A, EMR3, DHRS7B, and CEACAM8;
   wherein said measuring comprises detection and quantification of mRNA in the sample, and wherein said subject is identified as having an increased risk of mortality when said i) increase in expression and said ii) decrease in expression is present; and
   treating said subject identified as having an increased risk of mortality, wherein the treating comprises administering an appropriate treatment regimen selected from the group consisting of: administering an antibiotic, hydration, transfusion of blood products, vasopressors, ventilator assistance, and combinations thereof.

2. The method of claim 1, wherein said measuring further comprises measuring differential expression of additional genes selected from the group consisting of ARHGAP25, ASCL2, BIN1, CBFA2T3, CCL5, CD300A, CD5, CDK10, CLEC10A, CSK, CST3, CTDSP2, CX3CR1, DGCR2, DHRS7B, DOK2, FRAT2, HIST1H3H, HLA-DPA1, HSPA6, IL6R, ITGB1, ITPA, KCNJ2, KLHL21, LDLRAP1, LY86, MNDA, MTMR11, MXD4, PGRMC1, PKIA, PLEKHA1, POLR2C, POLRMT, PPM1F, RCBTB2, RIN1, RNF31, TARBP2, TBC1D22A, TGFBI, TST, ZDHHC7, APOL2, CD1D, CD3G, EMR3, FCER1A, RASSF4, ARID5B, BPI, CCNB1, CD24, CEACAM8, CENPF, CEP55, CKS2, CTSG, DDIT4, GYPA, HIPK2, KIAA0101, KIF14, MLF1IP, MPO, NEK2, NUSAP1, PDE4D, PLK1, POLD3, PRC1, PSAT1, RAB11FIP2, RHAG, SHCBP1, SPTA1, TOP2A, TRIB1, YES1, BIRC5, CASC5, MKI67, TUBG1, and combinations thereof.

3. The method of claim 1, wherein said measuring comprises or is preceded by one or more steps of: purifying cells from said sample, breaking the cells of said sample, and isolating RNA from said sample.

4. The method of claim 1, wherein said measuring comprises semi-quantitative PCR and/or nucleic acid probe hybridization.

5. The method of claim 1, wherein said platform comprises an array platform, a thermal cycler platform, a hybridization and multi-signal coded detector platform, a nucleic acid mass spectrometry platform, a nucleic acid sequencing platform, or a combination thereof.

6. The method of claim 1, wherein the subject is suffering from symptoms of sepsis and/or is suspected of having sepsis.

* * * * *

UNITED STATES PATENT AND TRADEMARK OFFICE
CERTIFICATE OF CORRECTION

PATENT NO. : 11,286,525 B2
APPLICATION NO. : 16/478202
DATED : March 29, 2022
INVENTOR(S) : Tsalik et al.

Page 1 of 1

It is certified that error appears in the above-identified patent and that said Letters Patent is hereby corrected as shown below:

In the Specification

Column 1, Line 7: Please correct "This application claims" to read -- This application is a 35 U.S.C. § 371 national phase application of International Application Serial No. PCT/US2018/013832, filed January 16, 2018, which claims --

Signed and Sealed this
Twenty-seventh Day of September, 2022

Katherine Kelly Vidal
*Director of the United States Patent and Trademark Office*